(12) United States Patent
Nakamura et al.

(10) Patent No.: US 12,031,930 B2
(45) Date of Patent: Jul. 9, 2024

(54) GAS SENSOR

(71) Applicant: Panasonic Intellectual Property Management Co., Ltd., Osaka (JP)

(72) Inventors: Kunihiko Nakamura, Osaka (JP); Masaki Fujikane, Osaka (JP); Kouhei Takahashi, Osaka (JP); Naoki Tambo, Kyoto (JP); Yasuyuki Naito, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 364 days.

(21) Appl. No.: 17/396,653

(22) Filed: Aug. 6, 2021

(65) Prior Publication Data

US 2021/0364458 A1 Nov. 25, 2021

Related U.S. Application Data

(63) Continuation of application No. PCT/JP2019/037207, filed on Sep. 24, 2019.

(30) Foreign Application Priority Data

May 21, 2019 (JP) ................................. 2019-095145

(51) Int. Cl.
*G01N 27/02* (2006.01)
*G01N 33/00* (2006.01)

(52) U.S. Cl.
CPC .......... *G01N 27/02* (2013.01); *G01N 33/0027* (2013.01)

(58) Field of Classification Search
CPC ....... H01L 2224/73265; H01L 23/3107; H01L 23/34; H01L 21/02513; H01L 31/02016;
(Continued)

(56) References Cited

U.S. PATENT DOCUMENTS 4,953,387 A * 9/1990 Johnson ................. G01N 27/12
73/25.03
6,786,076 B2 * 9/2004 Raisanen ............... G01N 27/12
73/25.05
(Continued)

FOREIGN PATENT DOCUMENTS

| JP | 7-198644 | 8/1995 |
| JP | 2007-024509 | 2/2007 |
| JP | 2010-060481 A | 3/2010 |

OTHER PUBLICATIONS

English Translation of Chinese Search Report dated Sep. 29, 2023 for the related Chinese Patent Application No. 201980089839.8.
(Continued)

*Primary Examiner* — Vinh P Nguyen
(74) *Attorney, Agent, or Firm* — Rimon P.C.

(57) ABSTRACT

A gas sensor includes a substrate, a support layer, a base layer, a heater layer disposed on or above the base layer, a gas sensing layer that is disposed on or above one of the heater layer and the base layer and that has a gas concentration dependent electrical impedance, and a detection electrode that is electrically connected to the gas sensing layer and that detects the impedance of the gas sensing layer. The substrate has a cavity and an opening formed by the cavity. The support layer is disposed on the substrate so as to cover at least an entire periphery of the opening. The base layer is supported by the support layer above the cavity so as to be separated from the substrate. A portion of the support layer in contact with the cavity has a first phononic crystal structure structured by a plurality of regularly arranged through-holes.

15 Claims, 19 Drawing Sheets

(58) Field of Classification Search
CPC ... H01L 31/024; H01L 27/1266; H01L 33/62; H01L 21/02433; H01L 23/66; H01L 23/3192; H01L 27/1218; H01L 2924/09701; H01L 21/02428; H01L 21/02532; H01L 21/02603; H01L 21/0262; H01L 2224/73267; H01L 24/24; H01L 33/647; G01R 33/0354; G01N 27/02; G01N 33/0031

See application file for complete search history.

(56) References Cited

U.S. PATENT DOCUMENTS

| | | | | |
|---|---|---|---|---|
| 6,997,040 | B1 * | 2/2006 | Lee | G01N 27/12 73/31.05 |
| 7,963,147 | B2 * | 6/2011 | Jun | G01N 27/128 73/25.05 |
| 9,236,552 | B2 | 1/2016 | Carr | |
| 9,599,945 | B2 * | 3/2017 | Jeran | G03G 15/5091 |
| 9,618,490 | B2 * | 4/2017 | Paik | G01N 33/0027 |
| 11,067,554 | B2 * | 7/2021 | Kim | G01N 33/0027 |
| 11,193,904 | B2 * | 12/2021 | Carr | H10N 10/10 |
| 2014/0076024 | A1 | 3/2014 | Duraffourg et al. | |
| 2014/0079091 | A1 | 3/2014 | Ruellan et al. | |
| 2016/0155923 | A1 | 6/2016 | Dubois et al. | |
| 2017/0356806 | A1 | 12/2017 | Takahashi et al. | |
| 2019/0107502 | A1 | 4/2019 | Carr | |

OTHER PUBLICATIONS

International Search Report of PCT application No. PCT/JP2019/037207 dated Jan. 7, 2020.

Tokuya Suzuki et al., "Development of an Ultra-Low Power MEMS Gas Sensor", Journal of the Society of Instrument and Control Engineers, vol. 57, No. 4, Apr. 2018, pp. 287-290.

K. Nakamura et al., "Determination of Low Concentration of Multi-target Gas Species Exhaled with the Breath", ECS Transactions, 75 (16) 83-90 (2016).

Kory F. Gray et al., "A MEMS Infrared Thermopile with Phononic Crystal Structures and Carbon Nanotube Absorption Layer", 2016 IEEE Sensors, Oct. 30, 2016, pp. 1-3, DOI: 10. 1109/ICSENS. 2016. 7808771, ISBN 978-1-4799-8287-5.

* cited by examiner

GAS SENSOR

CROSS-REFERENCE TO RELATED APPLICATIONS

This is a continuation application of International Application No. PCT/JP2019/037207, with an international filing date of Sep. 24, 2019, which claims priority of Japanese Patent Application No.: 2019-095145 filed on May 21, 2019, the content of which is incorporated herein by reference.

BACKGROUND

1. Technical Field

The present disclosure relates to a gas sensor.

2. Description of the Related Art

Gas sensors can be used to detect leaks in gas piping and to monitor the concentration of carbon monoxide or oxygen, for example. A typical existing gas sensor is a semiconductor sensor using an oxide semiconductor, such as tin oxide ($SnO_2$), (refer to, for example, Japanese Unexamined Patent Application Publication No. 7-198644). In such a sensor, for example, $SnO_2$ is heated to about 400° C. by an electric current heater encapsulated in a sintered $SnO_2$ body. At this temperature, the oxygen bonded to the $SnO_2$ can react with a target gas having a reducing character. Therefore, as the concentration of the target gas increases under the elevated temperature, the oxygen desorption from $SnO_2$ proceeds more easily and, thus, the electrical impedance of $SnO_2$ decreases. By associating the impedance of $SnO_2$ with the concentration of the target gas, the function of a gas sensor can be obtained.

A methane gas sensor using a thin $SnO_2$ film is described in Takuya Suzuki et al, "Development of Ultra-Low Power MEMS Gas Sensor", Journal of the Society of Instrument and Control Engineers, Vol. 57, No. 4, April 2018, pp. 287-290 (hereinafter, referred to as NPL 1). In the gas sensor, the power consumption is reduced by the following two methods:

1. to reduce the heat capacity by using an $SnO_2$ thin film, and
2. to heat the gas for a short time using a pulse current.

The heater power consumption of the hydrogen sensor SB-19, which is a kind of semiconductor gas sensor available from Nissha FIS, Inc., is 120 mW. In contrast, the gas sensor described in NPL 1 uses a thin film and a pulse current drive technique so as to achieve heating within tens of milliseconds and average power consumption less than or equal to 0.1 mW.

In general, semiconductor gas sensors have different detection sensitivities in accordance with different target gas species. For example, a sensor with greater sensitivity to hydrogen than to other gas species can be used as a hydrogen sensor. In gas sensors, gases other than the target gas are called interference gases. In an environment containing a large amount of interference gas, the detection accuracy of the target gas tends to decrease. A mufti-sensor technology that uses a plurality of gas sensors having different detection sensitivities when interference gases are contained is described in K. Nakamura, et al, "Determination of Low Concentration of Multi-Target Gas Species Exhaled with the Breath", ECS Transactions, vol. 75, issue 16, pp. 83-90, 2016. In the multi-sensor technology, multivariate analysis is applied to the response values obtained from the multiple gas sensors to estimate the concentration of each of the gas species including the target gas.

SUMMARY

A gas sensor with low power consumption enables, for example, a continuous gas monitoring operation by battery. However, the reduction of power consumption by the technology described in NPL 1 is still insufficient. In addition, a further reduction of power consumption is required for multi-sensor technology.

One non-limiting and exemplary embodiment provides a technique for a further reduction of power consumption in gas sensors.

In one general aspect, the techniques disclosed here feature a gas sensor including a substrate, a support layer, a base layer, a heater layer disposed on or above the base layer, a gas sensing layer disposed on or above one of the heater layer and the base layer, where the gas sensing layer has an electrical impedance that is gas concentration dependent, and a detection electrode electrically connected to the gas sensing layer, where the detection electrode detects the impedance of the gas sensing layer. The substrate has a cavity. The substrate has an opening formed by the cavity in plan view. The support layer is disposed on the substrate so as to cover at least an entire periphery of the opening. The base layer is supported by the support layer above the cavity so as to be separated from the substrate. The support layer has a first phononic crystal structure in a portion in contact with the cavity, and the first phononic crystal structure is structured by a plurality of regularly arranged through-holes.

According to the present disclosure, for example, a gas sensor with further reduced power consumption can be achieved.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1A:
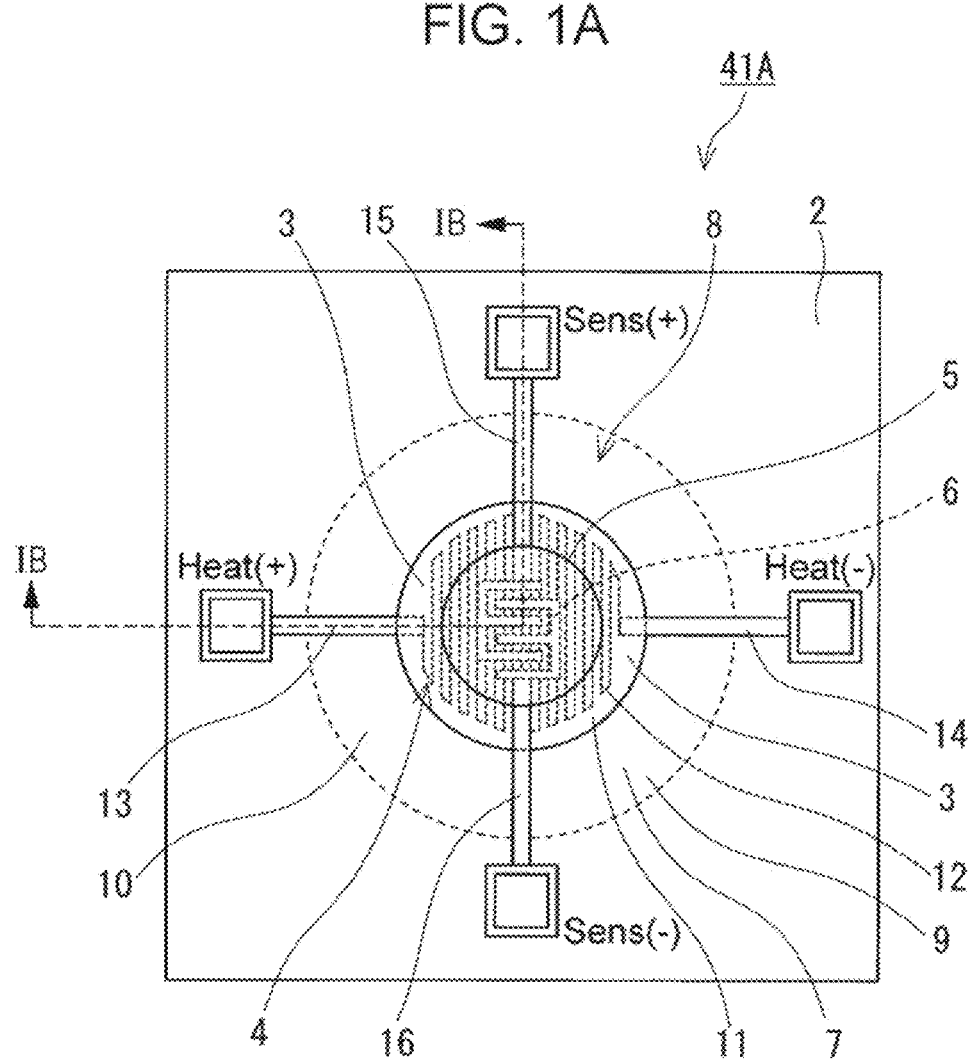
FIG. 1A is a plan view schematically illustrating a gas sensor according to a first embodiment.

Underlying Knowledge Forming Basis of the Present Disclosure

In a gas sensor according to the present disclosure, a gas sensing layer and a heater layer that heats the gas sensing layer are disposed apart from a substrate via a support layer and a base layer. The support layer has a phononic crystal structure in a portion that is in contact with a cavity and that is separated from the substrate. The phononic crystal structure is structured by a plurality of regularly arranged through-holes.

In insulators and semiconductors, heat is mainly carried by lattice vibrations called phonons. The thermal conductivity of a material (an insulator or a semiconductor) is determined by the dispersion relation of the phonons that the material has. The phonon dispersion relation refers to the relation between the frequency and wavenumber or refers to the band structure. In insulators and semiconductors, the heat-carrying phonons are in a wide frequency range of 100 GHz to 10 THz. This frequency band is the thermal band. The thermal conductivity of a material is determined by the dispersion relation of the phonons in the thermal band.

According to the phononic crystal structure, the dispersion relation of the phonons in the material can be controlled by the periodic structure of the through-holes. In other words, the thermal conductivity itself of the material can be controlled by the phononic crystal structure. In particular, the formation of a phononic band gap (PBG) by the phononic crystal structure can significantly reduce the thermal conductivity of the material. A phonon cannot exist in PBGs. Therefore, a PBG located in the thermal band can serve as a gap for heat conduction. In addition, a PBG can reduce the slope of the phonon dispersion curve in frequency bands other than a PBG. The reduction of the slope decreases the group velocity of phonons, which in turn decreases the heat conduction velocity. These factors contribute significantly to the reduction of the thermal conductivity of the material. The thermal conductivity of a material can be reduced, for example, by porosity. This is because the voids introduced by porosity reduce the thermal conductivity of the material. However, the phononic crystal structure can reduce the thermal conductivity of the material itself. Therefore, it is expected that the phononic crystal structure further reduces the thermal conductivity compared to mere porosity.

In the gas sensor according to the present disclosure, a phononic crystal structure that can significantly reduce thermal conductivity is applied to the gas sensing layer and the support structure of the heater layer. This application makes it possible to reduce the heat flow from the heated gas sensing layer toward the substrate. As a result, it is possible to raise the temperature of the gas sensing layer to the desired temperature with low power and, thus, a gas sensor that can be driven with low power consumption can be achieved.

Embodiments of Present Disclosure

Exemplary embodiments are described below with reference to the accompanying drawings.

Gas Sensor

First Embodiment

Figure 1B:
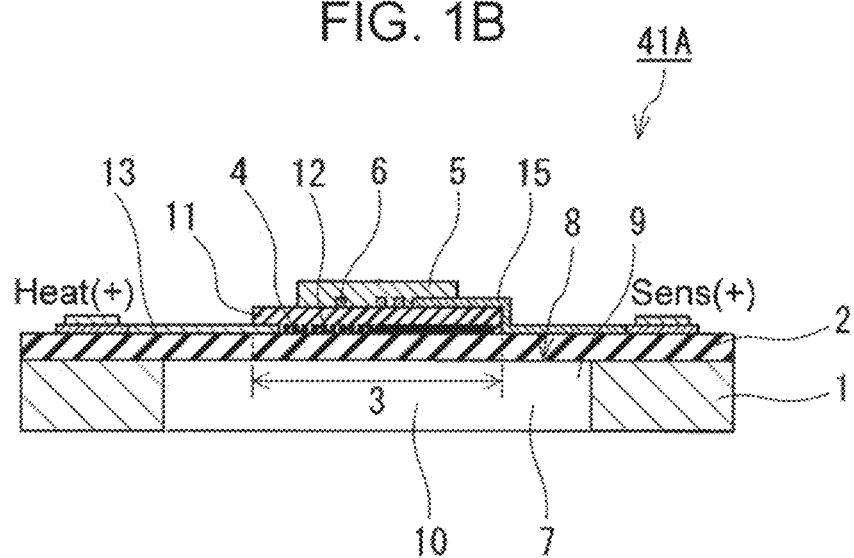
FIG. 1B is a cross-sectional view of the gas sensor taken along line IB-IB of FIG. 1A.
Figure 2A:
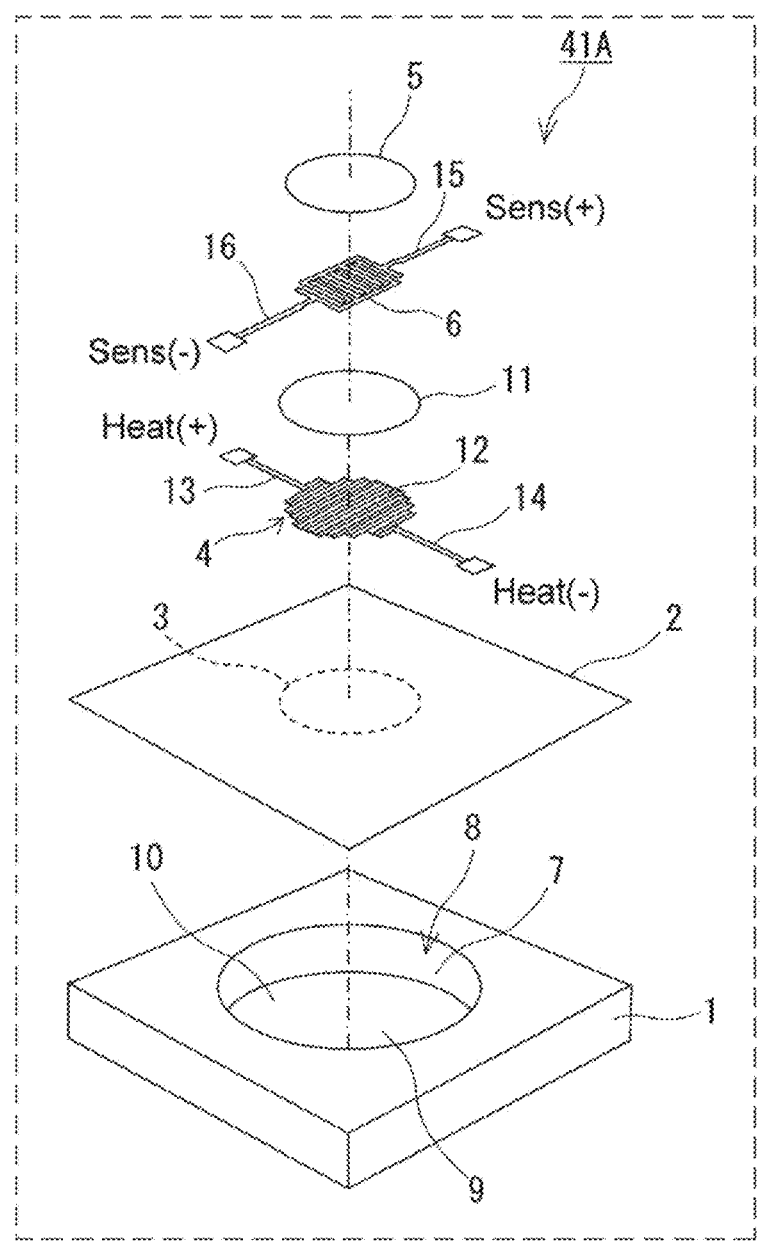
FIG. 2A is an exploded perspective view of the gas sensor illustrated in FIG. 1A.
Figure 2B:
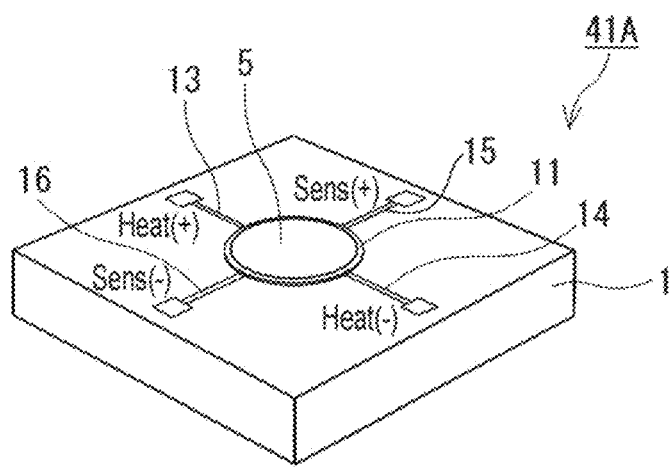
FIG. 2B is a perspective view of the gas sensor illustrated in FIG. 1A.

A gas sensor 41A according to the first embodiment is illustrated in FIGS. 1A and 1B and FIGS. 2A and 2B. FIG. 1B is a cross-sectional view of the gas sensor 41A taken along line IB-IB of FIG. 1A. FIG. 2A is an exploded perspective view of the gas sensor 41A. FIG. 2B is a perspective view of the gas sensor 41A. The gas sensor 41A comprises a substrate 1, a support layer 2, a base layer 3, a heater layer 4, a gas sensing layer 5, and a detection electrode 6.

The gas sensing layer 5 has an electrical impedance (hereinafter simply referred to as an "impedance") that is gas concentration dependent. The impedance of the gas sensing layer 5 can vary in accordance with the concentration of the target gas around the gas sensing layer 5. The gas sensing layer 5 contains a sensitive material having an impedance that varies in accordance with the concentration of the target gas. An example of a sensitive material is an oxide semiconductor. Examples of an oxide semiconductor include $SnO_2$, $TiO_2$, $WO_3$, and $Fe_2O_3$. The gas sensing layer 5 may be an oxide semiconductor layer. Alternatively, the gas sensing layer 5 may be a $SnO_2$ layer, a $TiO_2$ layer, a $WO_3$ layer, or an $Fe_2O_3$ layer. Note that the gas sensing layer 5 is not limited to the above-described examples. The gas sensing layer 5 is disposed above the heater layer 4. The detection electrode 6 is electrically connected to the gas sensing layer 5. The detection electrode 6 is disposed on the lower principal surface of the gas sensing layer 5. The impedance of the gas sensing layer 5 can be detected by the detection electrode 6.

The substrate 1 has a cavity 7, which is a through-hole that penetrates the substrate between both principal surfaces of the substrate 1. In plan view, the substrate 1 has an opening 8 formed by the cavity 7. The support layer 2 is provided on top of the substrate 1 so as to cover at least the entire periphery 9 of the opening 8. The support layer 2 in the example illustrated in FIGS. 1A to 2B covers the entire opening 8 including the periphery 9. The base layer 3 is supported by the support layer 2 so as to be located above the cavity 7 at a distance from the substrate 1. In cross-sectional view, the base layer 3 is sandwiched by the cavity 7 and the heater layer 4. A stacked body including the heater layer 4 and the gas sensing layer 5 is provided on top of the base layer 3. The heater layer 4 and the gas sensing layer 5 are suspended above the cavity 7 by the support layer 2 and the base layer 3 in a state where the heater layer 4 and the gas sensing layer 5 are separate from the substrate 1. This suspension structure restricts the heat flow from the heated gas sensing layer 5 toward the substrate 1. Note that the base layer 3 in the example illustrated in FIGS. 1A to 2B is part of the support layer 2. The base layer 3 can be defined as a region of the support layer 2 in which members to be suspended by the support layer 2 at a distance from the substrate 1 are disposed. The members include at least the heater layer 4 and the gas sensing layer 5.

The heater layer 4 comprises a resistance heating wire 12. The heater layer 4 generates heat by Joule heating due to an electric current flowing through the resistance heating wire 12. The resistance heating wire 12 of the gas sensor 41A is meandered. In the meander wiring, the wire density uniformity in the gas sensing layer 5 can be improved. In this manner, the effect of uniformly raising the temperature of the gas sensing layer 5 can be obtained. However, the wiring pattern of the resistance heating wire 12 is not limited to the above-described example.

The gas sensor 41A further includes a first interconnection wire 13 and a second interconnection wire 14 that are electrically connected to the resistance heating wire 12 so as to supply an electric current to the resistance heating wire 12. The first interconnection wire 13 is connected to one end of the resistance heating wire 12. The second interconnection wire 14 is connected to the other end of the resistance heating wire 12. The first interconnection wire 13 is electrically connected to a terminal Heat(+) at the end opposite to the end connected to the resistance heating wire 12. The second interconnection wire 14 is electrically connected to the terminal Heat(−) at the end opposite to the end connected to the resistance heating wire 12. The terminals Heat(−) and Heat(−) are disposed on the support layer 2. In plan view, the positions at which the terminals Heat(−) and Heat(−) are disposed on the support layer 2 do not overlap with the cavity 7. The heater layer 4 generates heat by an electric current flowing from the terminal Heat(+) to the terminal Heat(−) via the first interconnection wire 13, the resistance heating wire 12, and the second interconnection wire 14. The electric current may be a pulse current. However, the manner in which each of the first and second interconnection wires 13 and 14 is connected to the resistance heating wire 12 and the configuration of supplying an electric current to the resistance heating wire 12 are not limited to the above-described example.

In the gas sensor 41A, the heater layer 4 and the gas sensing layer 5 are disposed so as to overlap each other in plan view. In addition, the gas sensing layer 5 is disposed above the heater layer 4. The gas sensing layer 5 may be disposed on the heater layer 4. These configurations increase the efficiency of heating the gas sensing layer 5.

In the gas sensor 41A, the heater layer 4 and the detection electrode 6 are disposed so as to overlap each other in plan view. In addition, the detection electrode 6 is disposed above the heater layer 4. The gas sensor 41A further comprises an electrically insulating layer 11 provided between the heater layer 4 and the detection electrode 6. The electrically insulating layer 11 can ensure electrical insulation between the heater layer 4 and the detection electrode 6. In the example illustrated in FIGS. 1A to 2B, the electrically insulating layer 11 is disposed on the support layer 2 and the heater layer 4, and the detection electrode 6 and the gas sensing layer 5 are disposed on the electrically insulating layer 11. In the gas sensor 41A, the base layer 3 can be defined as a region of the support layer 2 in which the electrically insulating layer 11, which is a member having the largest area in plan view among the heater layer 4, the gas sensing layer 5, the detection electrode 6, and the electrically insulating layer 11, is disposed.

The detection electrode 6 is composed of a pair of comb electrodes that are combined. The gas sensor 41A further includes a third interconnection wire 15 and a fourth interconnection wire 16 that are electrically connected to the detection electrode 6 and transmit a detection signal output from the detection electrode 6. The third interconnection wire 15 is connected to one of the pair of comb electrodes. The fourth interconnection wire 16 is connected to the other comb electrode. The third interconnection wire 15 is electrically connected to a terminal Sens(−) at the end opposite to the end connected to the detection electrode 6. The fourth interconnection wire 16 is electrically connected to a terminal Sens(−) at the end opposite to the end connected to the detection electrode 6. The terminal Sens(−) and the terminal Sens(−) are disposed on the support layer 2. In plan view, the positions at which the terminals Sens(+) and Sens(−) are disposed on the support layer 2 do not overlap with the cavity 7. The impedance of the gas sensing layer 5 can be detected by a detection signal transmitted from the terminal Sens(+) to the detection electrode 6 via the third interconnection wire 15 and a detection signal transmitted from the detection electrode 6 to the terminal Sens(−) via the fourth interconnection wire 16. However, the configuration of the detection electrode 6, the manner in which the third interconnection wire 15 and fourth interconnection wire 16 are connected to the detection electrode 6, and the configuration for detecting the impedance of the gas sensing layer 5 are not limited to the above-described example.

The first interconnection wire 13, the second interconnection wire 14, the third interconnection wire 15, and the fourth interconnection wire 16 are formed radially from the center of the gas sensor 41A in plan view. The angle formed by the adjacent interconnection wires is 90 degrees in plan view. However, the angle is not limited to 90 degrees.

Figure 3A:
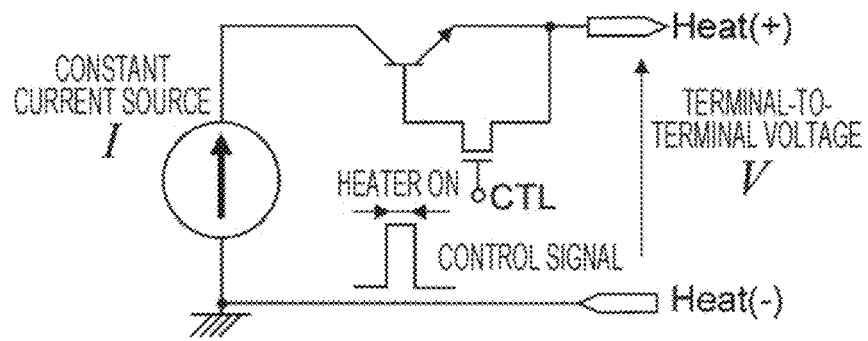
FIG. 3A is a circuit diagram illustrating an example of the circuit configuration for supplying an electric current to a heater layer.

An example of the circuit configuration for supplying an electric current to the heater layer 4 is illustrated in FIG. 3A. In the example illustrated in FIG. 3A, a pulse of a control signal corresponding to the switch-on of the heater is input to a control terminal CTL of an electrical switch. Only for a time period during which the pulse is input, a current I from a constant current source is supplied between the terminals Heat(+) and Heat(−). The supplied electric current is a pulse current. The width of the pulse, the interval between the pulses, and the value of the current I can be determined such that the temperature of the gas sensing layer 5 reaches a predetermined set value. In the case where the gas sensing layer 5 is made of $SnO_2$, the set temperature is, for example, 400° C. However, the set temperature is not limited to the temperature in this example. The temperature may be set to any value at which the sensitivity to the desired target gas is maximized. If the gas sensing layer 5 is a thin film, control may be performed so that the heater is switched off when the temperature of the gas sensing layer 5 reaches the set value. In general, the thin-film gas sensing layer 5 has a small heat capacity. For this reason, the time period during which the temperature of the gas sensing layer 5 continuously rise after the heater is switched off is very small. Thus, even the above-described control can ensure a high measurement accuracy.

Figure 3B:
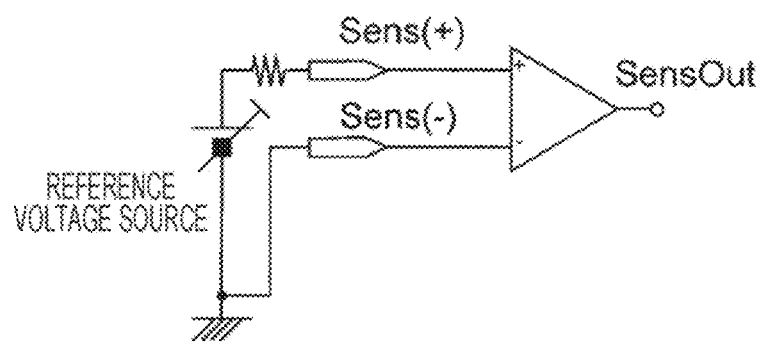
FIG. 3B is a circuit diagram illustrating an example of a detection circuit that detects the impedance of a gas sensing layer.
Figure 3C:
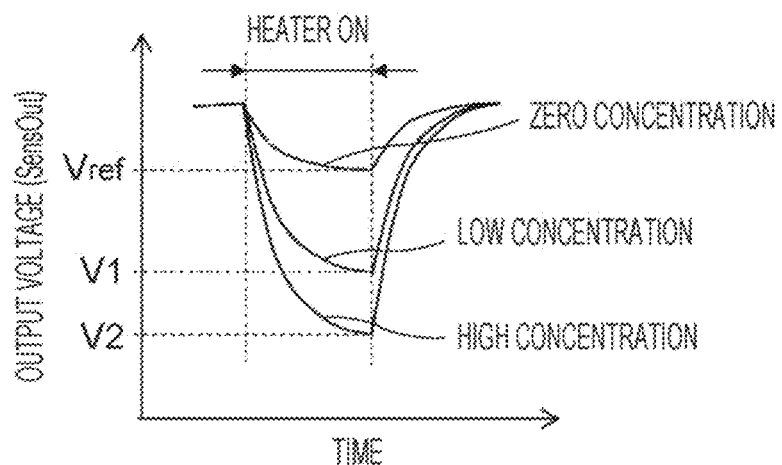
FIG. 3C is a graph illustrating an example of an output signal output from a differential amplifier when the impedance of the gas sensing layer is detected.

An example of a detection circuit that detects the impedance of the gas sensing layer 5 is illustrated in FIG. 3B. In the example illustrated FIG. 3B, an electric current is applied between a pair of comb electrodes from a reference voltage source. A change in the impedance between the two comb electrodes is transmitted as a detection signal, and the change appears in the form of a potential difference between the terminals Sens(+) and Sens(−). The generated potential difference can be read and output by a differential amplifier. An example of an output signal from the differential amplifier is illustrated in FIG. 3C. As illustrated in FIG. 3C, the impedance of the gas sensing layer 5 decreases with increasing temperature, caused by the switch-on of the heater. Here, the higher the concentration of the target gas, the greater a decrease in impedance. Therefore, the output voltage V2 in the case of high concentration is lower than the output voltage V1 in the case of low concentration. By storing an output voltage Vref when the concentration of the target gas is zero, the output voltage differences Vref−V1 and Vref−V2 can be the information associated with the concentration of the target gas.

The substrate 1 is composed of a semiconductor material, for example. An example of a semiconductor material is silicon (Si). The substrate 1 may be formed of a plurality of layers. An oxide film may be formed on the surface of the substrate 1 having the support layer 2 disposed thereon.

In plan view, the opening 8 of the cavity 7 is circular in shape. In addition, in plan view, the periphery 9 is a ring in shape. However, the shapes of the opening 8 and the periphery 9 are not limited to the above-described examples.

The cavity 7 of the gas sensor 41A is formed by a through-hole 10. In this configuration, stagnation of gas in the cavity 7 is reduced. The gas is, for example, gas that has passed through through-holes of the support layer 2 having the phononic crystal structure. If the gas sensing layer 5 is sensitive to the stagnant gas, the sensitivity of the gas sensor 41A may decrease, or false detection may occur. These problems can be prevented by providing a path for enabling the gas that may stagnate in the cavity 7 to escape below the gas sensor 41A.

The support layer 2 and the base layer 3 are usually formed of an insulating material. Examples of an insulating material include oxides, such as $SiO_2$, and nitrides, such as SiN. The thickness of the support layer 2 and the base layer 3 is, for example, 0.05 µm to 1 µm. The base layer 3 may be part of the support layer 2. In plan view, the shape of the support layer 2 of the gas sensor 41A is the same as the shape of the substrate 1. In addition, the shape of the base layer 3 is a circle in plan view. However, the shapes of the support layer 2 and the base layer 3 are not limited to the above-described examples.

The thickness of the gas sensing layer 5 is, for example, 0.05 µm to 1 µm. The gas sensing layer 5 having a thickness within the above-described range can be the thin film. However, the thickness of the gas sensing layer 5 is not limited to the above-described example. For example, the thickness of a gas sensing layer 5 obtained by sintering powders can be greater than or equal to 1 µm.

Each of the detection electrode 6, the first interconnection wire 13, the second interconnection wire 14, the third interconnection wire 15, and the fourth interconnection wire 16 is usually formed of a conductive material. Examples of a conductive material include metals, such as platinum (Pt), tungsten (W), and titanium (Ti), and crystalline semiconductors, such as polycrystalline silicon (poly-Si) and polycrystalline silicon germanium (poly-SiGe). To prevent heat transfer via each of the interconnection wires, the conductive material may be a non-metal. The first interconnection wire 13 and/or the second interconnection wire 14 may be formed of the same material as the heater layer 4. The third interconnection wire 15 and/or the fourth interconnection wire 16 may be formed the same material as the detection electrode 6. The thickness of these materials is, for example, 0.1 µm to 1 µm. As used herein, the term "crystalline semiconductor," refers to a semiconductor in which the content of the crystallized base material is, for example, greater than or equal to 50 mass %, greater than or equal to 70 mass %, greater than or equal to 80 mass %, greater than or equal to 90 mass %, or even greater than or equal to 95 mass %. In "crystalline semiconductor," the content of the crystallized base material may be 100 mass %. The content of the crystallized base material can be evaluated, for example, by X-ray diffraction.

Examples of an insulating material of the electrically insulating layer 11 is the same as the material of the support layer 2 and the base layer 3. The thickness of the electrically insulating layer 11 is, for example, 0.1 µm to 1 µm.

The terminals Heat(+), Heat(−), Sens(+) and Sens(−) are usually formed conductive materials. Examples of a conductive material is the same as the examples of a conductive material of the detection electrode 6 and the interconnection wires. Each of the terminals may have a metal deposited thereon for wire bonding. An example of the metal is aluminum (Al).

The support layer 2 has a first phononic crystal structure structured by a plurality of regularly arranged through-holes in the portion in contact with the cavity 7. The support layer 2 may have the first phononic crystal structure in part of the portion in contact with the cavity 7 or in the entire portion. In addition, the support layer 2 may have the first phononic crystal structure in the portion other than the portion in contact with the cavity 7. The support layer 2 illustrated in FIG. 1A to FIG. 2B has the first phononic crystal structure in the entire portion in contact with the cavity 7. The through-holes of the phononic crystal structure typically extend in the thickness direction of the layer. The through-holes may extend in a direction perpendicular to the principal surfaces of the layer.

In the gas sensor 41A, the members other than the support layer 2 may have a phononic crystal structure. In this case, the heat flow from the heated gas sensing layer toward the substrate can be reduced more.

For example, the gas sensing layer 5 may have a second phononic crystal structure structured by a plurality of regularly arranged through-holes. The gas sensing layer 5 illustrated in FIG. 1A to FIG. 2B has the second phononic crystal structure. The gas sensing layer 5 having the phononic crystal structure can block a heat flow that propagates in the gas sensing layer 5 in the in-plane direction and, thereafter, propagates from the periphery thereof to the substrate 1 via the support layer 2 and/or the electrically insulating layer 11. Note that the phononic crystal structure does not significantly block the propagation of heat in the direction in which the through-holes extend (which is usually the thickness direction of the layer). For this reason, the heater layer 4 can increase the temperature of even the gas sensing layer 5 having a phononic crystal structure. In addition, in the gas sensing layer 5 having a phononic crystal structure, the through-holes can reduce the thermal stress at the interface between the gas sensing layer 5 and the electrically insulating layer 11 caused by the difference in thermal expansion coefficients between the two layers. As a result, the reliability of the gas sensor 41A can be increased.

For example, the heater layer 4 may have a third phononic crystal structure structured by a plurality of regularly arranged through-holes. The resistance heating wire 12 illustrated in FIG. 1A to FIG. 2B has the third phononic crystal structure.

For example, the first interconnection wire 13 and/or the second interconnection wire 14 may have a fourth phononic crystal structure structured by a plurality of regularly arranged through-holes. The first interconnection wire 13 and the second interconnection wire 14 illustrated in FIG. 1A to FIG. 2B have the fourth phononic crystal structure.

For example, the third interconnection wire 15 and/or the fourth interconnection wire 16 may have a sixth phononic crystal structure structured by a plurality of regularly arranged through-holes. The third interconnection wire 15 and fourth interconnection wire 16 illustrated in FIG. 1A to FIG. 2B have the sixth phononic crystal structure.

The phononic crystal structures that the members can have may be the same or different from one another.

The phononic crystal structure that each of the members can have may include a first domain and a second domain, which are phononic crystal regions. The first domain is formed of a plurality of through-holes regularly arranged in a first direction in plan view. The second domain is formed of a plurality of through-holes regularly arranged in a second direction that differs from the first direction in plan view. Hereinafter, the phononic crystal structure is referred to as a phononic crystal structure A. The first phononic crystal structure may be the phononic crystal structure A. Alternatively, at least one structure selected from the group consisting of the first phononic crystal structure, the second phononic crystal structure, the third phononic crystal structure, the fourth phononic crystal structure, a fifth phononic crystal structure (described below), and the sixth phononic crystal structure may be the phononic crystal structure A. The phononic crystal structure A is described below.

Figure 4:
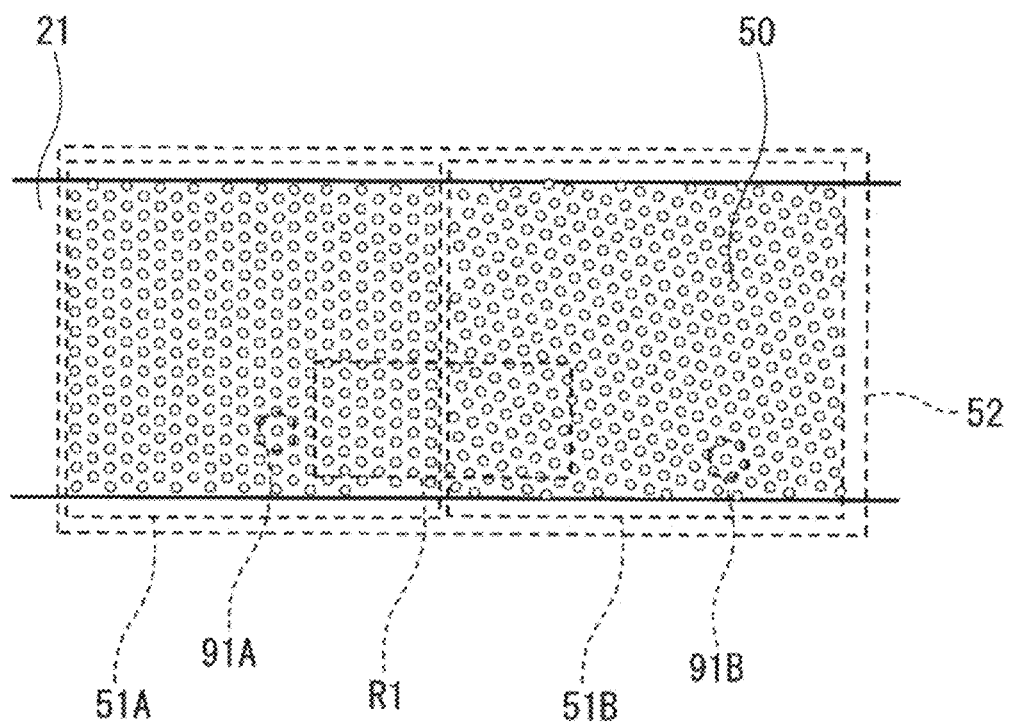
FIG. 4 is a plan view schematically illustrating an example of a phononic crystal structure that a gas sensor according to the present disclosure can have.

An example of the phononic crystal structure A is illustrated in FIG. 4. FIG. 4 is a plan view of a portion of a member 21 having the phononic crystal structure A. The member 21 is typically a layered member. The member 21 has a plurality of through-holes 50 extending in the thickness direction. The phononic crystal structure A illustrated in FIG. 4 is a two-dimensional phononic crystal structure in which the plurality of through-holes 50 are regularly arranged in the in-plane direction.

The phononic crystal structure A illustrated in FIG. 4 has a first domain 51A, which is a phononic crystal region, and a second domain 51B, which is a phononic crystal region. The first domain 51A is formed of a plurality of through-holes 50 regularly arranged in the first direction in plan view. The second domain 51B is formed of a plurality of through-holes 50 regularly arranged in the second direction that differs from the first direction in plan view. In each of the domains 51A and 51B, the diameters and the periods of arrangement of the plurality of through-holes 50 are the same. In addition, in the domains 51A and 51B, the orientations of the unit lattices 91A and 91B each of which is composed of a plurality of regularly arranged through-holes 50 are the same, respectively. Each of the domains 51A and 51B is also a phononic single crystal structure. The phononic crystal structure A illustrated in FIG. 4 is also a phononic polycrystalline structure 52, which is a composite of phononic single crystal structures. The shapes of the first domain 51A and the second domain 51B are rectangular in plan view. The shapes of the first domain 51A and the shape of the second domain 51B are the same in plan view.

As one example, the domain which is a phononic crystal region has an area of at least $25P^2$ in plan view (where P is period of arrangement of the through-holes 50). To control the phonon dispersion relation using the phononic crystal structure, the domain may have an area of at least $25P^2$. For a domain having a square shape in plan view, an area of at least $25P^2$ can be secured by setting the period to a value greater than or equal to 5×P.

Figure 5A:
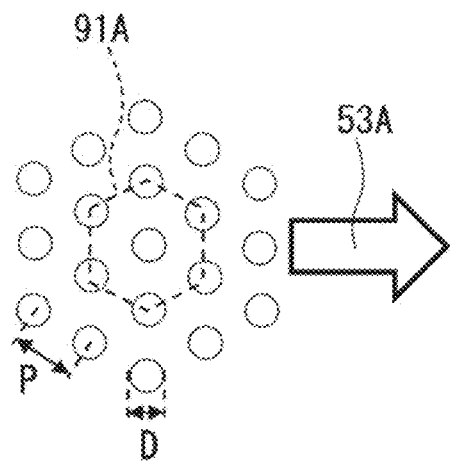
FIG. 5A is a schematic illustration of a unit lattice and its orientation in a first domain included in the phononic crystal structure illustrated in FIG. 4.
Figure 5B:
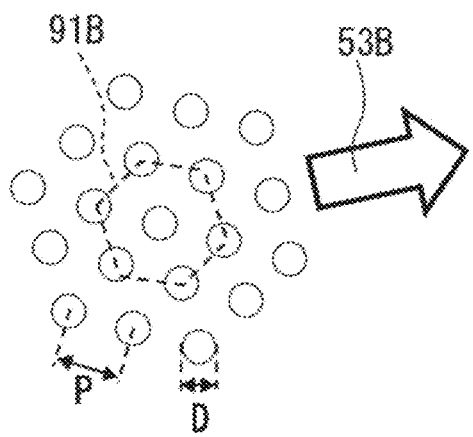
FIG. 5B is a schematic illustration of a unit lattice and its orientation in a second domain included in the phononic crystal structure illustrated in FIG. 4.

As illustrated in FIGS. 5A and 5B, in the phononic crystal structure A, an orientation 53A of the unit lattice 91A in the first domain 51A and an orientation 53B of the unit lattice 91B in the second domain 51B differ from each other in plan view. The angle formed by the orientations 53A and 53B is, for example, greater than or equal to 10 degrees in plan view. However, if the unit lattices 91A and 91B are the same and have n times rotational symmetry, the upper limit of the angle formed by the orientations 53A and 53B is less than 360/n degrees. Note that when the unit lattices have n times rotational symmetry for different numbers n, the largest n is used to define the upper limit of the above-mentioned angle.

For example, a hexagonal lattice has two times rotational symmetry, three-times rotational symmetry, and six-times rotational symmetry. In this case, the value 6 is used for n, which defines the upper limit of the angle. That is, for the hexagonal unit lattices 91A and 91B, the angle formed by the orientations 53A and 53B is less than 60 degrees. The phononic crystal structure A has at least two phononic crystal regions having different unit lattice orientations. As long as this condition is satisfied, the phononic crystal structure A may further include any phononic crystal region and/or any region not having a phononic crystal structure.

The orientation of the unit lattice can be determined on the basis of any rule. However, the orientation of a unit lattice needs to be determined by applying the same rule to different domains. For example, the orientation of the unit lattice is the direction of extension of the line bisecting the angle formed by two non-parallel sides that make up the unit lattice. Note that the two sides need to be determined by applying the same rule to different domains.

Figure 6:
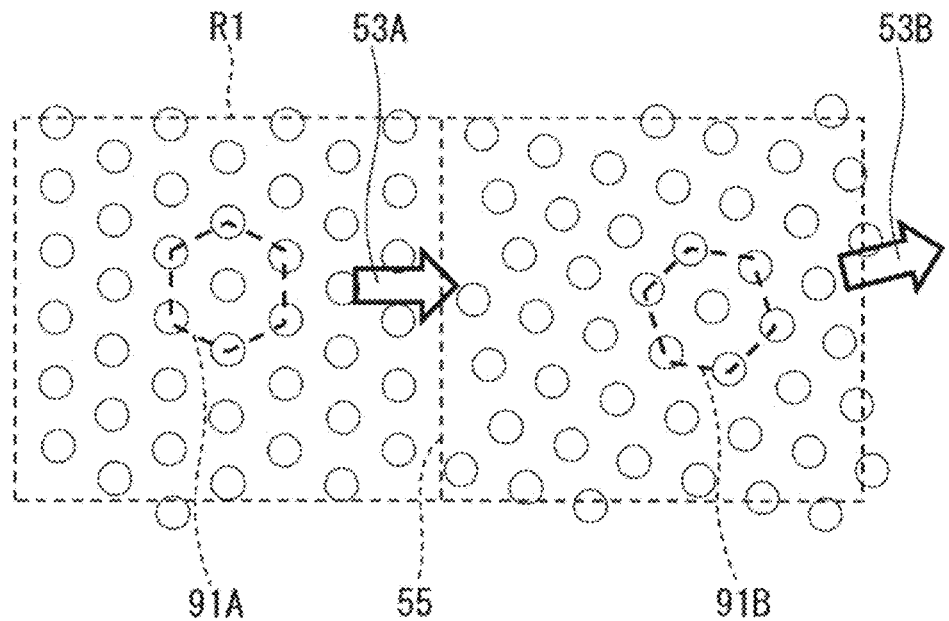
FIG. 6 is an enlarged view of a region R1 of the phononic crystal structure illustrated in FIG. 4.

FIG. 6 is an enlarged view of a region R1 of the phononic crystal structure A illustrated in FIG. 4. At an interface 55 between the adjacent first domain 51A and second domain 51B, each of the orientation 53A of the unit lattice 91A and the orientation 53B of the unit lattice 91B changes. The interface 55 at which the orientation of the unit lattice changes results in a large interfacial resistance to heat flowing macroscopically through the phononic crystal structure A. The interfacial resistance is based on mismatch in phonon group velocity that occurs between the first domain 51A and second domain 51B. The interfacial resistance contributes to a reduction in the thermal conductivity of the member 21 having the phononic crystal structure A. Note that the interface 55 illustrated in FIG. 6 extends in a straight line in plan view. In addition, the interface 55 extends in the width direction of the member 21 in plan view. The width direction can be perpendicular to the direction of extension of the centerline of the member 21, which is defined by the macro heat transfer direction. The interface 55 may divide the phononic crystal structure A perpendicularly to the macro heat transfer direction in plan view.

In the phononic crystal structure A illustrated in FIG. 4, the period P of arrangement of the plurality of through-holes 50 in the first domain 51A is the same as the period P of arrangement of the plurality of through-holes 50 in the second domain 51B.

In the phononic crystal structure A illustrated in FIG. 4, the diameter of the plurality of regularly arranged through-holes 50 in the first domain 51A is the same as the diameter of the plurality of regularly arranged through-holes 50 in the second domain 51B.

In the phononic crystal structure A illustrated in FIG. 4, the type of unit lattice 91A in the first domain 51A is the same as the type of unit lattice 91B in the second domain 5B. The unit lattice 91A and the unit lattice 913 illustrated in FIG. 4 are both hexagonal lattices.

There is no limit to the shape of each domain in plan view. Examples of the shape of each domain in plan view include a polygon including a triangle, a square, and a rectangle, a circle, an ellipse, or a composite shape thereof. The shape of each domain in plan view may be indefinite. In addition, there is no limit to the number of domains that phononic crystal structure A has. The effect of interfacial resistance due to the interface between domains increases with increasing number of domains that phononic crystal structure A has. Furthermore, there is no limit to the size of each domain that phononic crystal structure A has.

Figure 7:
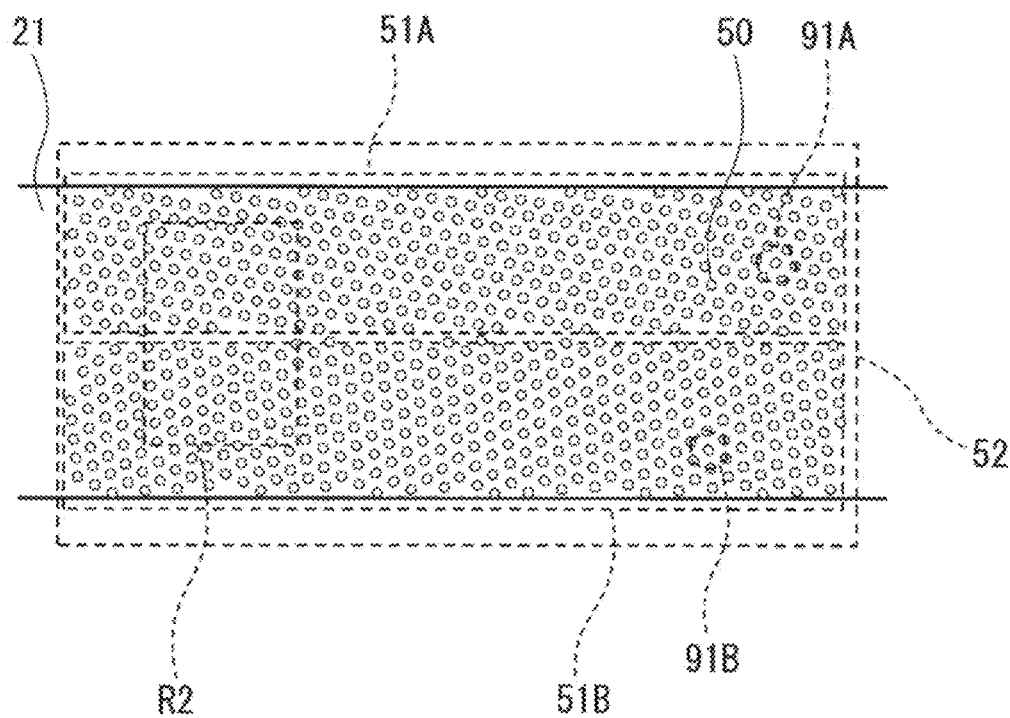
FIG. 7 is a plan view schematically illustrating another example of a phononic crystal structure that a gas sensor according to the present disclosure can have.
Figure 8:
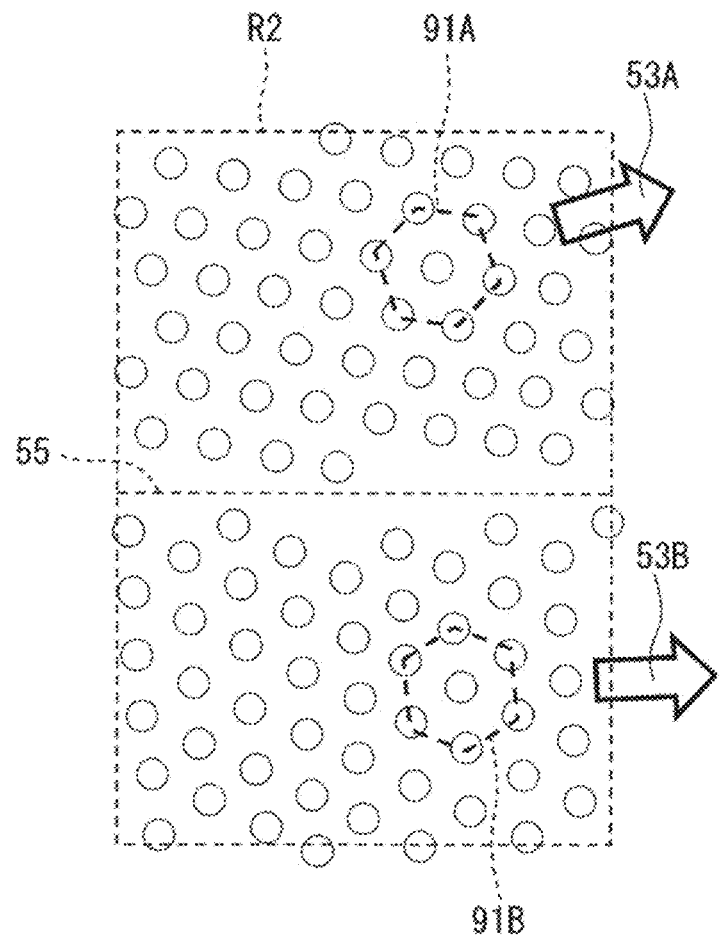
FIG. 8 is an enlarged view of a region R2 of the phononic crystal structure illustrated in FIG. 7.

The phononic crystal structure A illustrated in FIGS. 7 and 8 is the polycrystalline structure 52. In the polycrystalline structure 52 illustrated in FIGS. 7 and 8, the interface 55 between the adjacent first domain 51A and second domain 51B extends in the direction of the long side of the member 21 in plan view. The direction of the long side can be the macro heat transfer direction. Except for the feature, the phononic crystal structure A illustrated in FIGS. 7 and 8 has the same configuration as the phononic crystal structure A illustrated in FIG. 4. The interface 55 divides the phononic crystal structure A parallel to the macro heat transfer direction in plan view. Note that FIG. 8 is an enlarged view of the region R2 illustrated in FIG. 7.

In the phononic crystal structure A illustrated in FIGS. 4 and 7, the size of the first domain 51A and the size of the second domain 51B are the same in plan view. However, in plan view, the sizes of the first domain 51A and the second domain 51B of phononic structure A may differ from each other.

Figure 9:
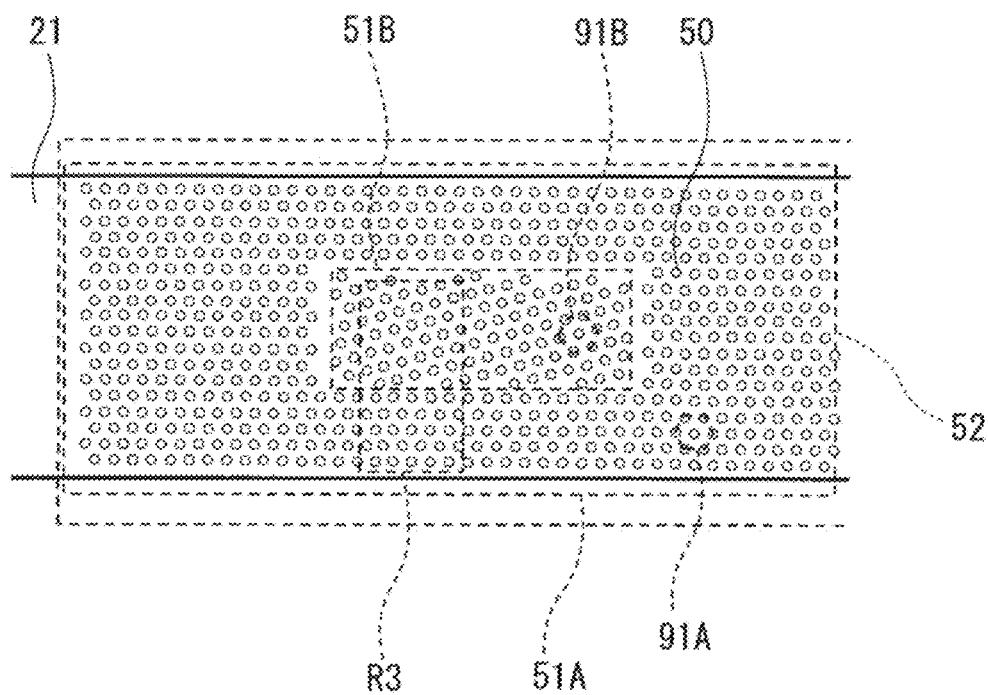
FIG. 9 is a plan view schematically illustrating still another example of a phononic crystal structure that a gas sensor according to the present disclosure can have.
Figure 10:
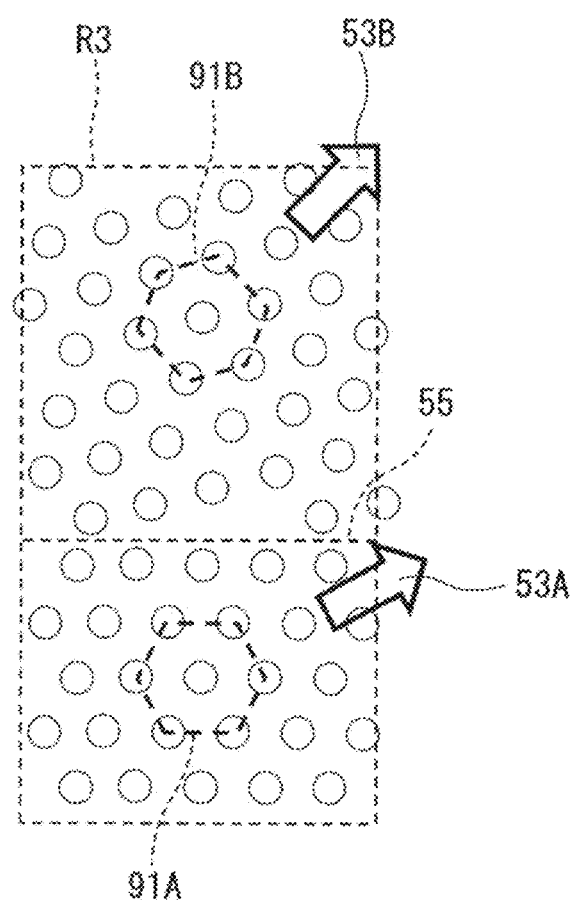
FIG. 10 is an enlarged view of a region R3 of the phononic crystal structure illustrated in FIG. 9.

The phononic crystal structure A illustrated in FIGS. 9 and 10 is the polycrystalline structure 52. In the polycrystalline structure 52 illustrated in FIGS. 9 and 10, the second domain 51B is surrounded by the first domain 51A in plan view. The shapes of the first domain 51A and the second domain 51B are rectangular in plan view. However, the size of the first domain 51A and the size of the second domain 51B differ from each other in plan view. The interface 55 between the second domain 51B and the first domain 51A surrounding the second domain 51B forms the outer edge of the second domain 51B in plan view. Except for the features, the phononic crystal structure A illustrated in FIGS. 9 and 10 has the same configuration as the phononic crystal structure A illustrated in FIG. 4. Note that FIG. 10 is an enlarged view of a region R3 illustrated in FIG. 9.

In the phononic crystal structure A illustrated in FIGS. 9 and 10, the interface 55 has a bent portion.

In addition, the phononic crystal structure A illustrated in FIGS. 9 and 10 has the second domain 51B that is not in contact with the outer periphery of the member 21.

Figure 11:
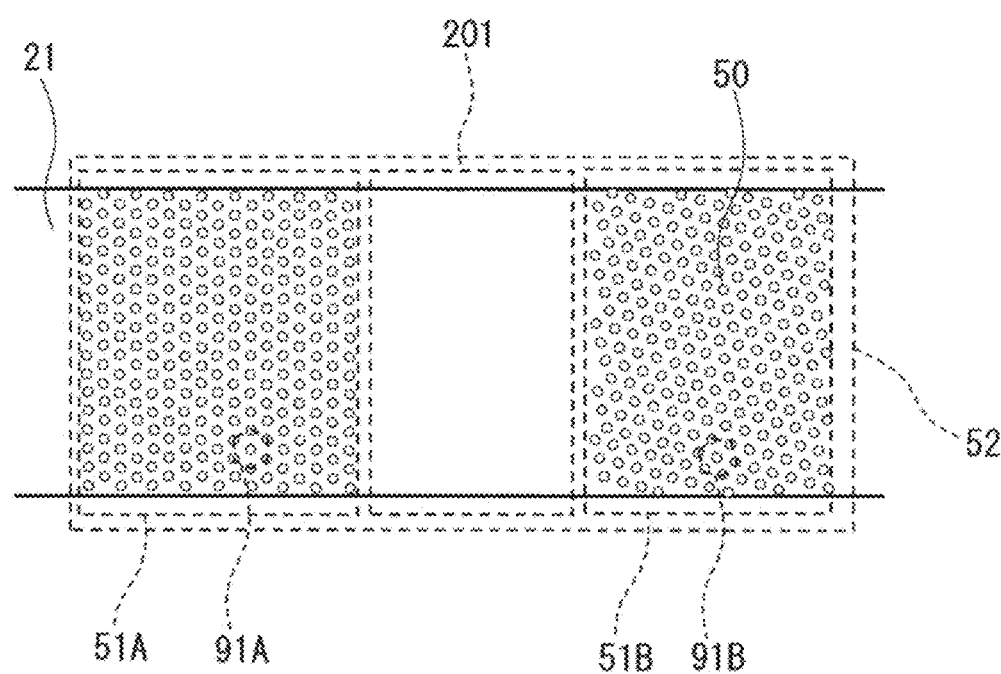
FIG. 11 is a plan view schematically illustrating yet still another example of a phononic crystal structure that a gas sensor according to the present disclosure can have.

The phononic crystal structure A illustrated in FIG. 11 is the polycrystalline structure 52. In the polycrystalline structure 52 illustrated in FIG. 11, the first domain 51A and the second domain 51B are disposed so as to be separated from each other in plan view. More specifically, in the plan view, a region 201 not having a through-hole 50 is provided between the first domain 51A and the second domain 51B. Except for the feature, the phononic crystal structure A illustrated in FIG. 11 has the same structure as the phononic crystal structure A illustrated in FIG. 4.

Figure 12:
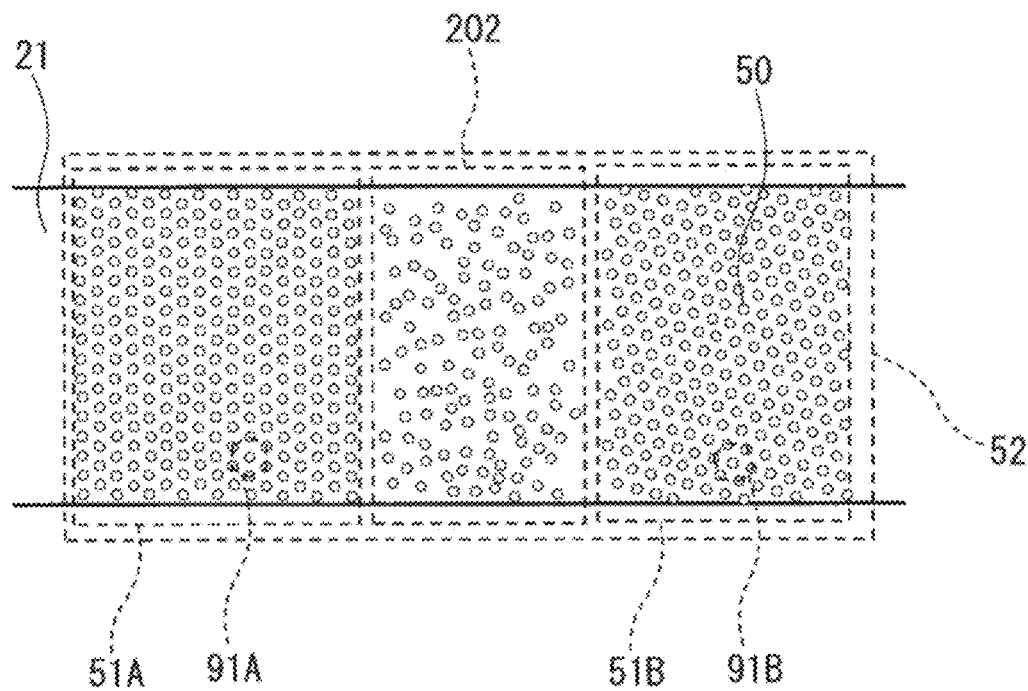
FIG. 12 is a plan view schematically illustrating yet still another example of a phononic crystal structure that a gas sensor according to the present disclosure can have.

The phononic crystal structure A illustrated in FIG. 12 is the polycrystalline structure 52. In the polycrystalline structure 52 illustrated in FIG. 12, the first domain 51A and the second domain 51B are disposed so as to be separated from each other in plan view. More specifically, a region 202 having randomly arranged through-holes 50 therein is provided between the first domain 51A and the second domain 51B in plan view. In the region 202, the through-holes 50 are not regularly arranged in plan view. Alternatively, the area of the region 202 in which the through-holes 50 are regularly arranged is, for example, less than $25P^2$ in plan view, where P is the period of the arrangement of the through-holes 50. Except for the feature, the phononic crystal structure A illustrated in FIG. 12 has the same structure as the phononic crystal structure A illustrated in FIG. 4.

Figure 13:
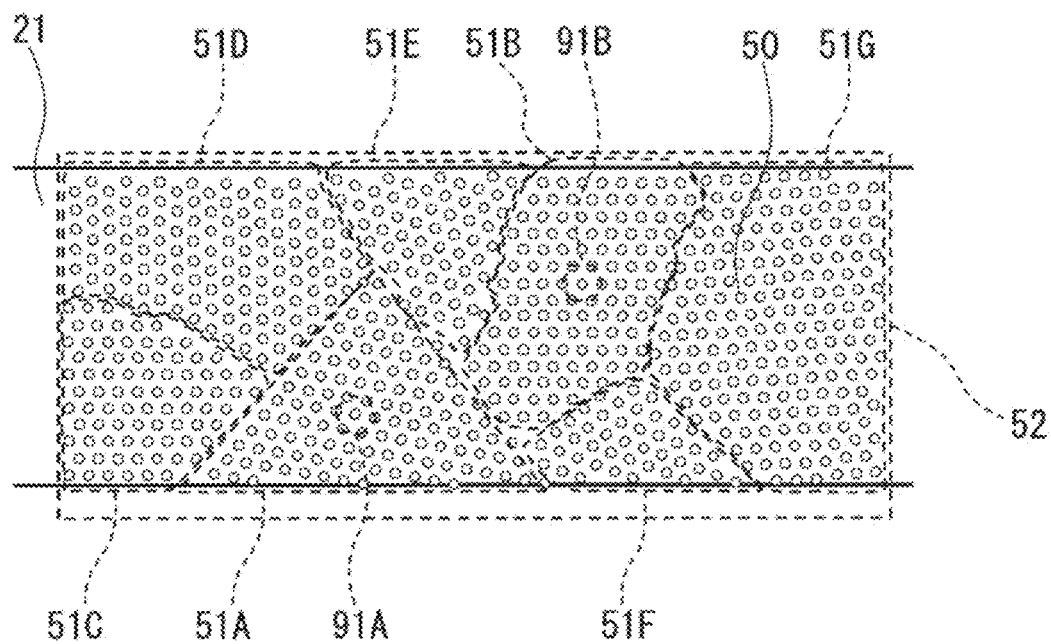
FIG. 13 is a plan view schematically illustrating yet still another example of a phononic crystal structure that a gas sensor according to the present disclosure can have.

The phononic crystal structure A illustrated in FIG. 13 is the polycrystalline structure 52. The polycrystalline structure 52 illustrated in FIG. 13 includes a plurality of domains having different shapes in plan view, that is, domains 51A, 51B, 51C, 51D, 51E, 51F and 51G. In each of the domains, the periods of the arrangement of the through-holes 50 and the orientations of the unit lattices are the same. However, among the domains 51A to 51G, the orientations of the unit lattices differ from one another. In addition, in plan view, the sizes and shapes of the domains 51A to 51G differ from one another. According to such a configuration, in the whole phononic crystal structure A, the number of orientations of the unit lattices is greater than that in the above-described examples of the configuration. For this reason, the effect of decreasing the thermal conductivity by changing the orientation of the unit lattice from domain to domain becomes more prominent. In addition, in this configuration, the interfaces 55 between domains extend in a plurality of random directions in plan view. For this reason, the effect of decreasing the thermal conductivity due to the interfacial resistance becomes more prominent.

Furthermore, in the phononic crystal structure A illustrated in FIG. 13, the interface 55 between the adjacent first domains 51A and second domain 51B extends in a direction at an angle to the width direction of the member 21 in plan view. In addition, the interface 55 has a bent portion in plan view.

Figure 14A:
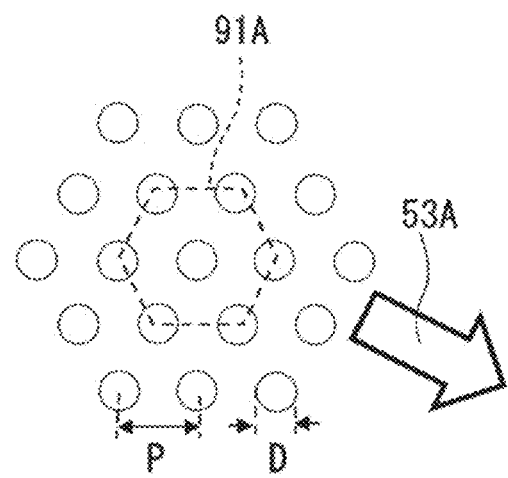
FIG. 14A is a schematic illustration of an example of a unit lattice of a phononic crystal structure that a gas sensor according to the present disclosure can have.
Figure 14B:
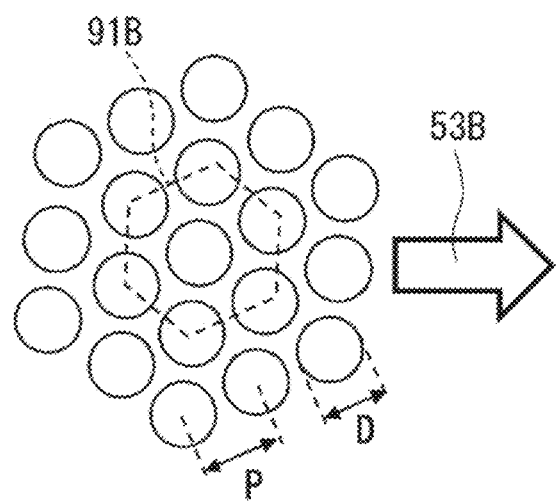
FIG. 14B is a schematic illustration of another example of a unit lattice of a phononic crystal structure that a gas sensor according to the present disclosure can have.

The polycrystalline structure 52, which is a phononic crystal structure A, may include a first domain 51A and a second domain 51B having different period P of the arrangement of the through-holes 50 and/or different diameter D of the through-holes 50 from each other. The diameter D of the through-holes 50 in the first domain 51A illustrated in FIG. 14A and the diameter D of the through-holes 50 in the second domain 51B illustrated in FIG. 14B differ from each other. The period P of the arrangement of the through-holes 50 in the first domain 51A illustrated in FIG. 14A is the same as the period P of the arrangement of the through-holes 50 in the second domain 51B illustrated in FIG. 14B.

Figure 15:
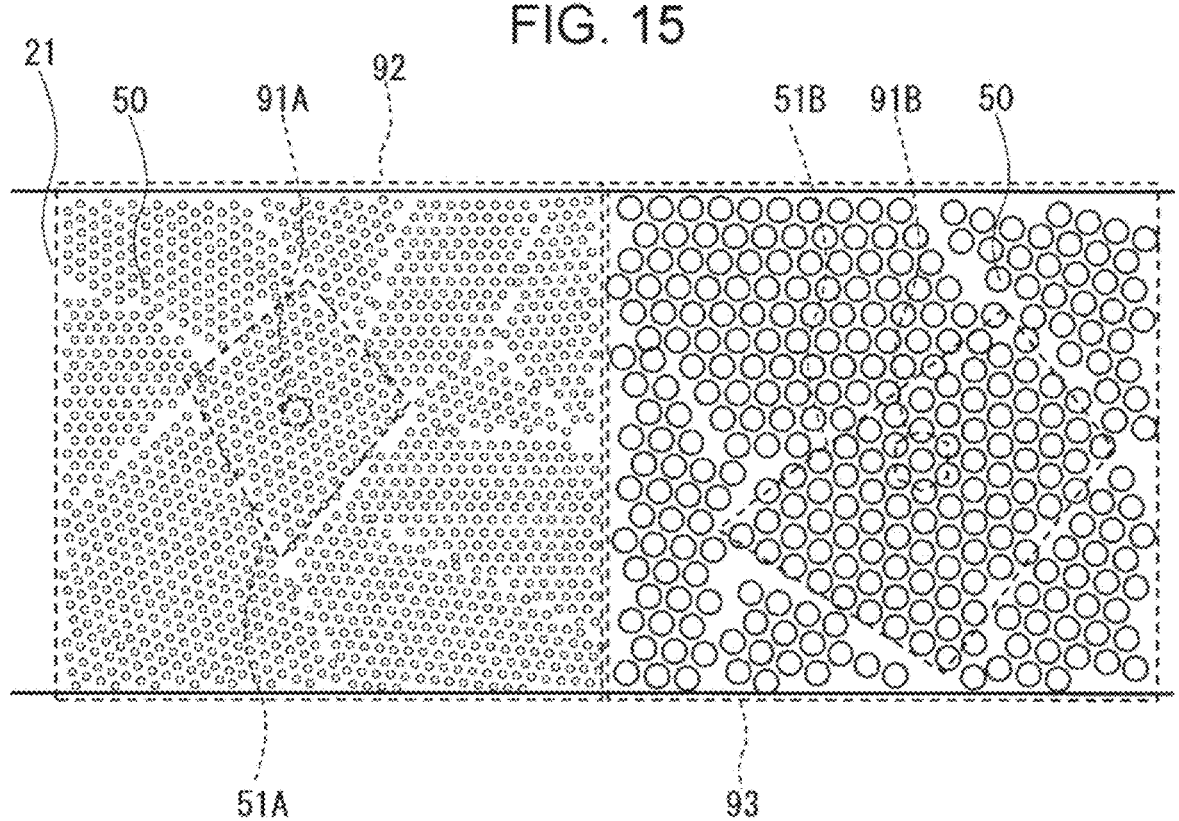
FIG. 15 is a plan view schematically illustrating another example of a phononic crystal structure that a gas sensor according to the present disclosure can have.

The phononic crystal structure A illustrated in FIG. 15 has a first domain 51A in which a plurality of through-holes 50 having relatively small period P and diameter D are regularly arranged and a second domain 51B in which a plurality of through-holes 50 having relatively large period P and diameter D are regularly arranged. In addition, the phononic crystal structure A illustrated in FIG. 15 has a region 92 structured by a plurality of through-holes 50 having relatively small period P and diameter D and a region 93 structured by a plurality of through-holes 50 having relatively large period P and diameter D. The region 92 and the region 93 are adjacent to each other. Similarly to the example illustrated in FIG. 13, the regions 92 and 93 each contain a plurality of domains that have different shapes in plan view and that have unit lattice orientations different from one another. In addition, the regions 92 and 93 can divide the phononic crystal structure A perpendicularly to the macro heat transfer direction. In this configuration, the frequency range of the phononic band gap formed of the first domain 51A differs from the frequency range of the phononic band gap formed of the second domain 51B, so that the effect of decreasing the thermal conductivity becomes particularly prominent.

Figure 16:
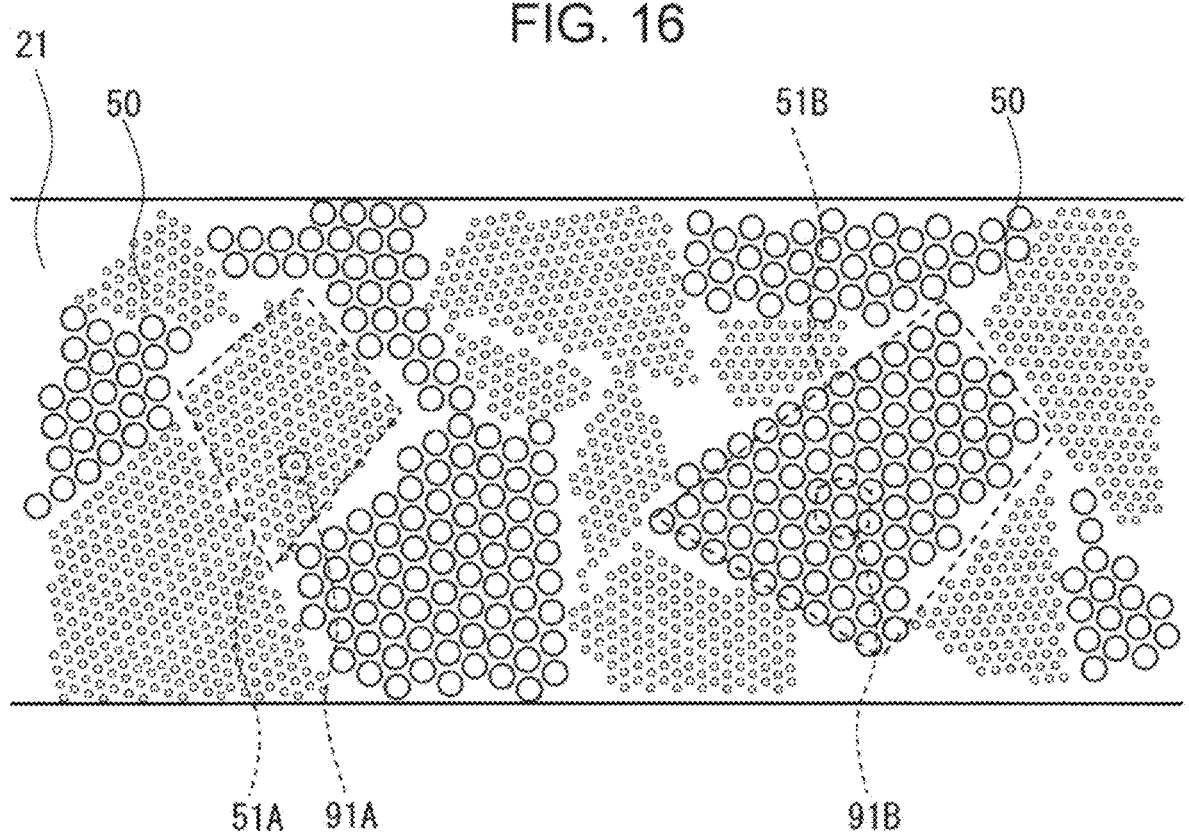
FIG. 16 is a plan view schematically illustrating still another example of a phononic crystal structure that a gas sensor according to the present disclosure can have.

The phononic crystal structure A illustrated in FIG. 16 includes a first domain 51A in which a plurality of through-holes 50 having relatively small period P and diameter D are regularly arranged and a second domain 51B in which a plurality of through-holes 50 having relatively large period P and diameter D are regularly arranged. The phononic crystal structure A illustrated in FIG. 16 includes a plurality of domains that have shapes different from one another in plan view and that have unit lattice orientations different from one another. In this configuration, the frequency range of the phononic band gap formed of the first domain 51A differs from the frequency range of the phononic band gap formed of the second domain 51B, so that the effect of decreasing the thermal conductivity becomes particularly prominent.

The period P of the arrangement of through-holes 50 is, for example, greater than or equal to 1 nm and less than or equal to 300 nm. This is because the wavelengths of the heat-carrying phonons mainly range from 1 nm to 300 nm. The period P is determined by the center-to-center distance between adjacent through-holes 50 in plan view (refer to FIGS. 14A and 14B).

As one example, a mathematical formula $D/P \geq 0.5$ is satisfied, where $D/P$ is a ratio of the diameter D of the through-hole 50 to the period P. If the ratio $D/P < 0.5$, the porosity of the member 21 may be excessively decreased and, thus, the thermal conductivity may not be sufficiently decreased. To prevent adjacent through-holes 50 from being in contact with each other, the upper limit of the ratio $D/P$ is less than 0.9, for example. The diameter D is the diameter of the opening of the through-hole 50. If the shape of the opening of the through-hole 50 is a circle in plan view, the diameter D is the diameter of the circle. The shape of the opening of the through-hole 50 does not necessarily have to be a circle in plan view. In this case, the diameter D is determined by the diameter of an imaginary circle having the same area as that of the opening (refer to FIGS. 14A and 14B).

Figure 17A:
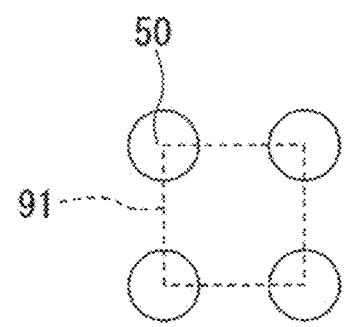
FIG. 17A is a schematic illustration of an example of a unit lattice of a phononic crystal structure that the gas sensor according to the present disclosure can have.
Figure 17B:
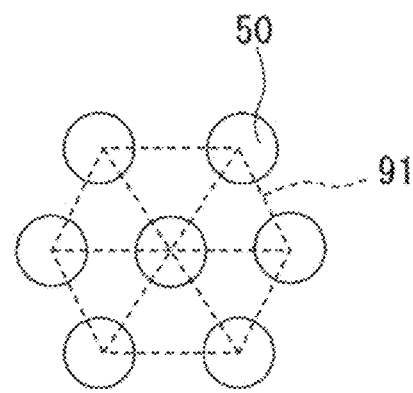
FIG. 17B is a schematic illustration of another example of a unit lattice of a phononic crystal structure that the gas sensor according to the present disclosure can have.
Figure 17C:
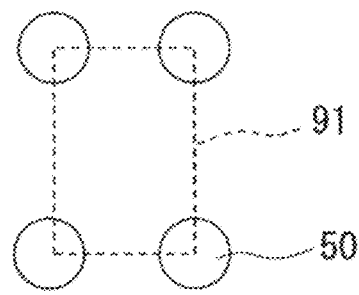
FIG. 17C is a schematic illustration of still another example of a unit lattice of a phononic crystal structure that the gas sensor according to the present disclosure can have.
Figure 17D:
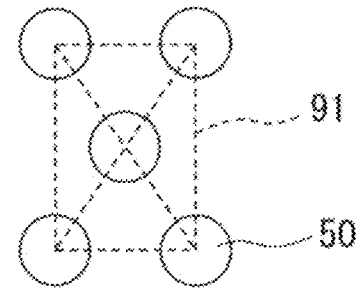
FIG. 17D is a schematic illustration of yet still another example of a unit lattice of a phononic crystal structure that the gas sensor according to the present disclosure can have.

The types of unit lattices 91 formed by a plurality of regularly arranged through-holes 50 include, but not limited to the following: a square lattice (FIG. 17A), a hexagonal lattice (FIG. 17B), a rectangular lattice (FIG. 17C), and a face-centered rectangular lattice (FIG. 17D) Note that the types of the unit lattice 91 are not limited to these examples.

The phononic crystal structure that each of the members can have is not limited to the above-described examples. The phononic crystal structure may be, for example, the structure described in Japanese Unexamined Patent Application Publication No. 2017-223644. However, the phononic crystal structure A with two or more phononic crystal regions having the orientations of unit lattices different from one another can decrease the thermal conductivity of the member 21 more, that is, can increase the heat insulation property more. The reason therefor is described below.

According to the study of the present inventors, the degree of decrease in thermal conductivity caused by the phononic crystal structure depends on the angle formed by the direction of heat transfer and the orientation of the unit lattice of the phononic crystal structure. This is because the factors related to heat conduction, such as the bandwidth of the PBG, the number of PBGs, and the average group velocity of phonons, depend on the angle. In addition, in terms of heat transfer from a macro perspective, phonons flow from high temperature to low temperature. In contrast, from a micro perspective, in a nano-scale region, the flow directions of phonons are not directional. In other words, from a micro perspective, the flow directions of phonons are not uniform. In a phononic crystal structure with multiple phononic crystal regions having uniformly aligned orientations of unit lattices, the interaction is maximized for phonons flowing in a certain particular direction, from a micro perspective. However, the interaction is weakened for phonons flowing in the other directions. In contrast, in a phononic crystal structure A with two or more phononic crystal regions having the orientations of unit lattices different from one another, the interaction can be strengthened for each of the phonons flowing in multiple directions, from a micro perspective. In this way, the thermal conductivity of the member 21 can be decreased more.

The through-holes of the phononic crystal structure may be filled with a material that differs from the material of a member having the structure. However, the material of the member and the other material need to be different in terms of thermal conductivity. If the through-holes of a phononic crystal structure are filled, gas permeation through the through-holes can be prevented.

Figure 18:
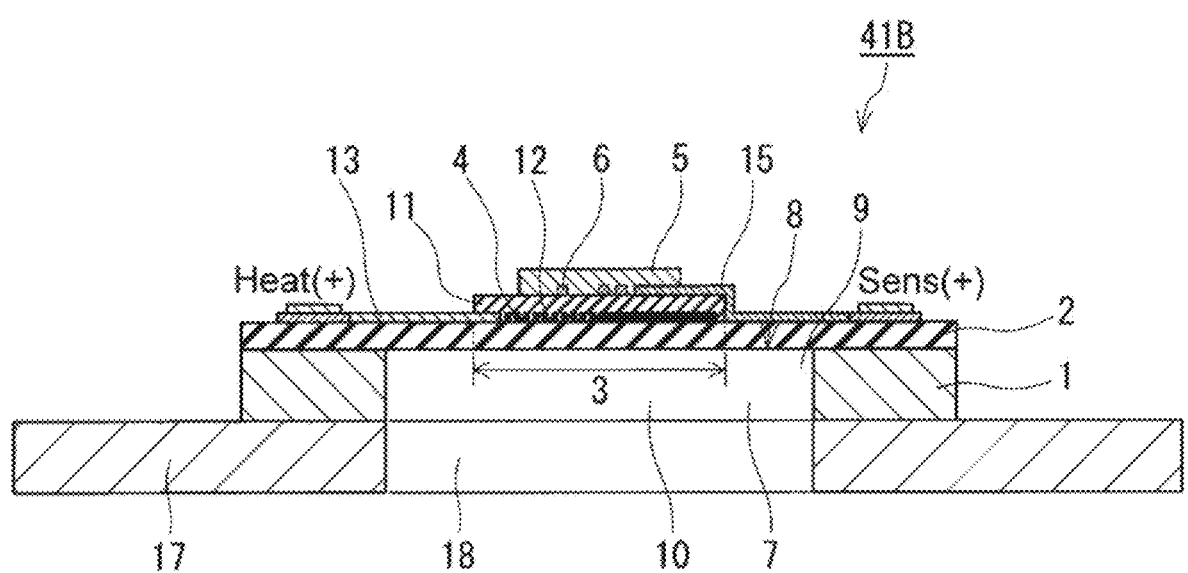
FIG. 18 is a schematic cross-sectional view of a modification of the gas sensor according to the first embodiment.

FIG. 18 illustrates a modification of the gas sensor 41A according to the first embodiment. A gas sensor 41B illustrated in FIG. 18 further includes a mounting substrate 17. The gas sensor 41A illustrated in FIG. 1A to FIG. 2B is mounted on the mounting substrate 17. The mounting substrate 17 has, formed therein, a through-hole 18 that connects both principal surfaces of the substrate. In plan view, the through-hole 10 of the substrate 1 and the through-hole 18 of the mounting substrate 17 overlap with each other. The through-hole 10 and the through-hole 18 may correspond to each other in plan view. The through-hole 10 and the through-hole 18 prevent stagnation of gas in the cavity 7.

Second Embodiment

Figure 19A:
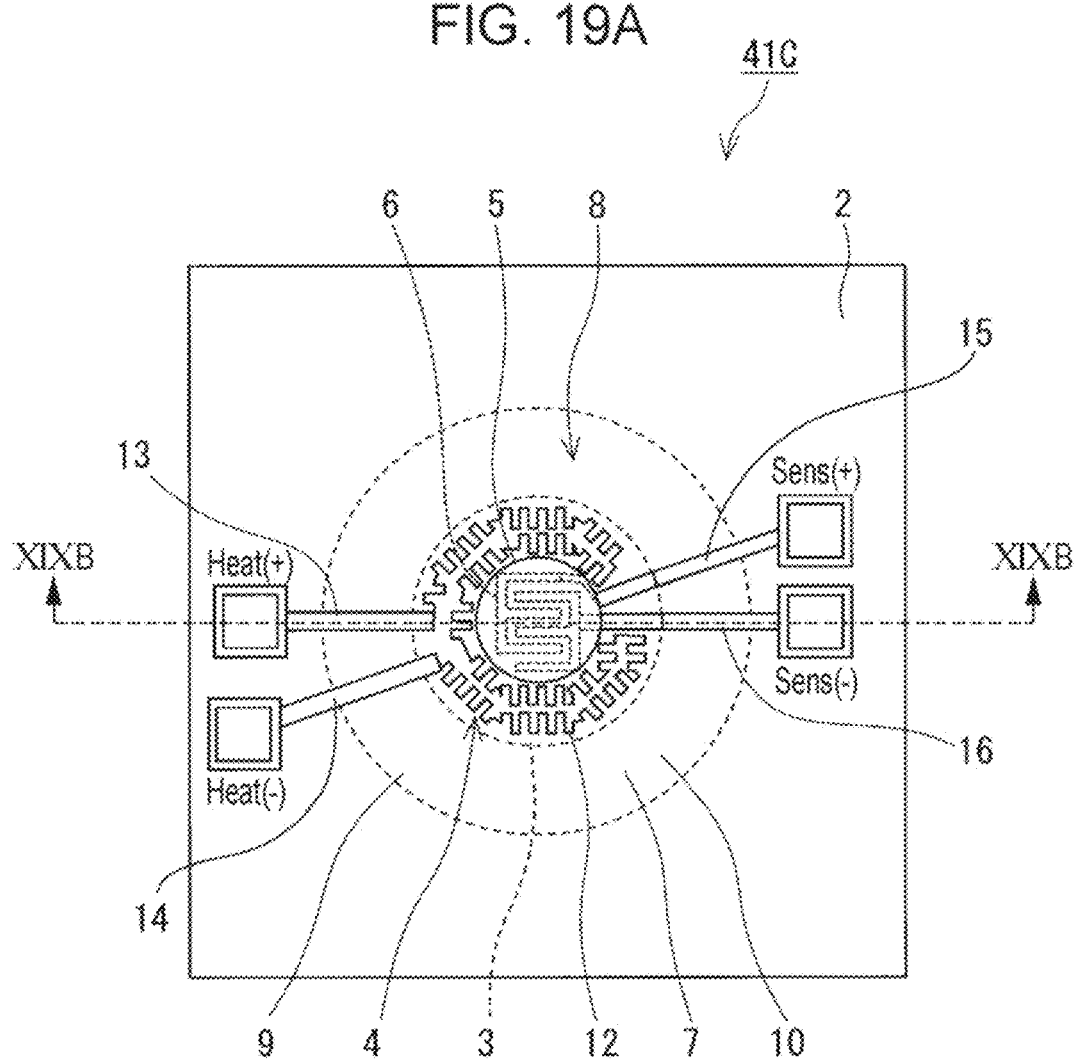
FIG. 19A is a plan view schematically illustrating a gas sensor according to a second embodiment.
Figure 19B:
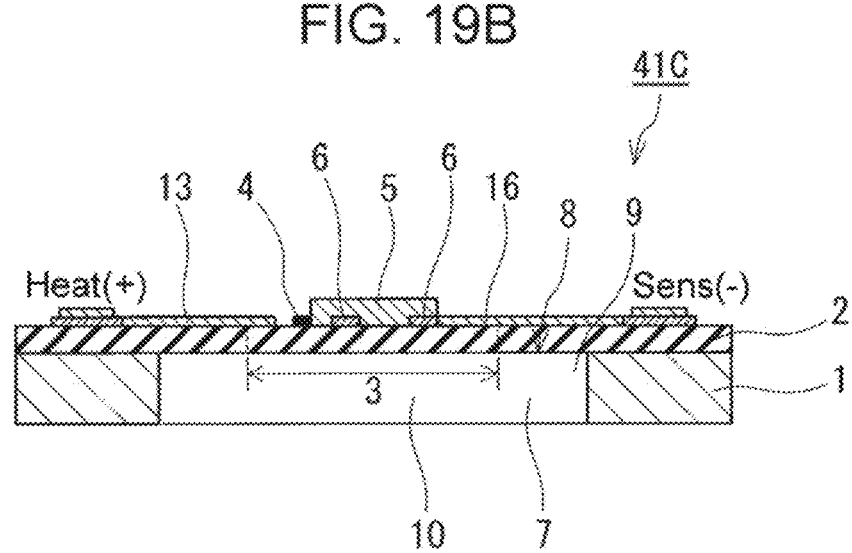
FIG. 19B is a cross-sectional view of the gas sensor taken along line XIXB-XIXB of FIG. 19A.

FIGS. 19A and 19B illustrate a gas sensor 41C according to the second embodiment, FIG. 19B is a cross-sectional view of the gas sensor 41C taken along line XIXB-XIXB of FIG. 19A. The gas sensor 41C has the same configuration as the gas sensor 41A according to the first embodiment, except for the arrangement of the gas sensing layer 5 and heater layer 4.

In the gas sensor 41C, the heater layer 4 is disposed around the gas sensing layer 5 in plan view. The gas sensing layer 5 and the heater layer 4 are not stacked, and the gas sensing layer 5 and the heater layer 4 do not overlap in plan view. Similarly, the detection electrode 6 is not stacked on the heater layer 4, and the detection electrode 6 does not overlap with the heater layer 4 in plan view. For this reason, the electrically insulating layer 11 can be removed from the gas sensor 41C. The heater layer 4 and the gas sensing layer 5 are formed on top of the base layer 3 so as to be in contact with the base layer 3. Compared with the gas sensor 41A, the gas sensor 41C can be manufactured at a lower cost so as to be compact in the stacking direction of the layers.

The base layer 3 of the gas sensor 41C can be defined as a region of the support layer 2 where the heater layer 4 is provided in plan view.

The base layer 3 of the gas sensor 41C does not necessarily have to have a phononic crystal structure. In this case, the heat of the heater layer 4 can be transferred to the gas sensing layer 5 more rapidly through the base layer 3.

Third Embodiment

Figure 20A:
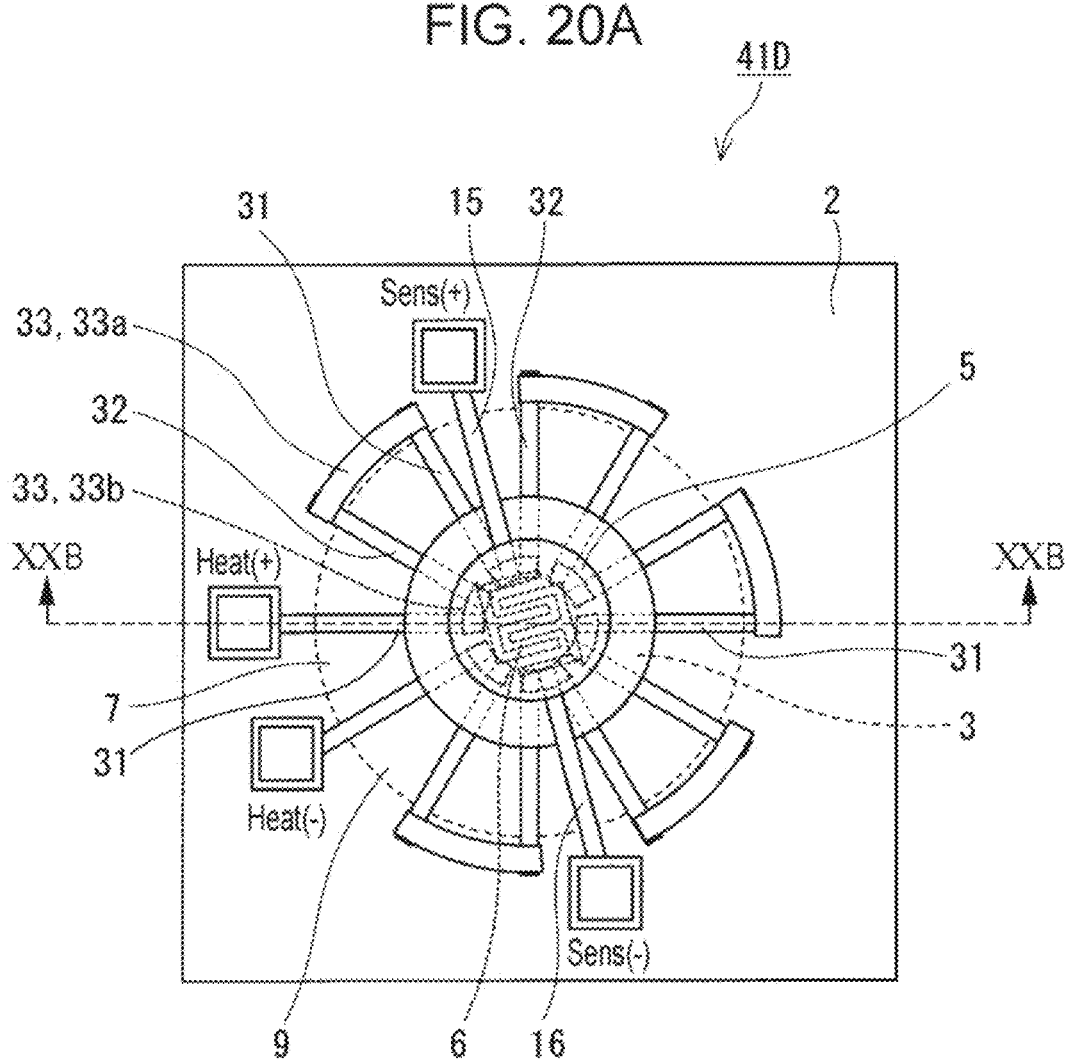
FIG. 20A is a plan view schematically illustrating a gas sensor according to a third embodiment.
Figure 20B:
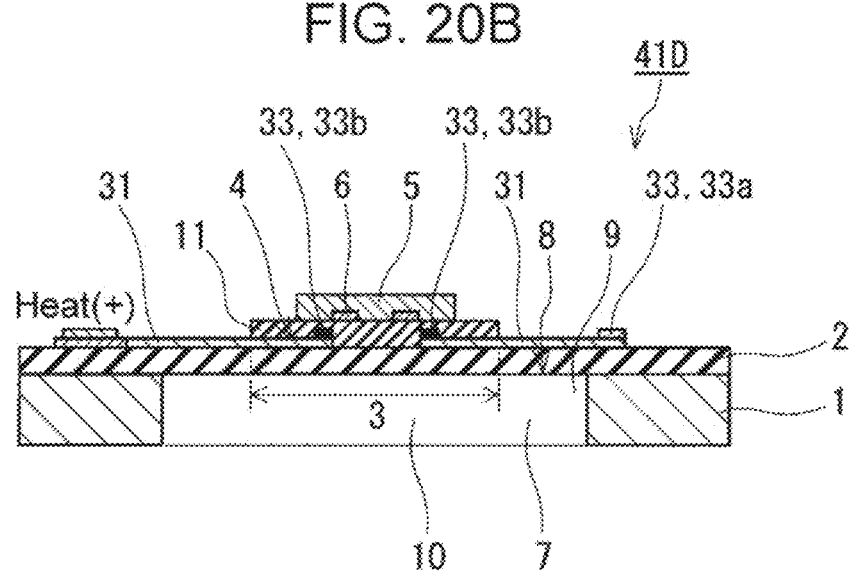
FIG. 20B is a cross-sectional view of the gas sensor taken along line XXB-XXB of FIG. 20A.

FIGS. 20A and 20B illustrate a gas sensor 41D according to the third embodiment. FIG. 20B is a cross-sectional view of the gas sensor 41D taken along line XXB-XXB of FIG. 20A. The gas sensor 41D has the same configuration as the gas sensor 41A according to the first embodiment, except for the configuration of the heater layer 4.

The heater layer 4 of the gas sensor 41D is a Peltier element layer comprising p-type interconnection wires 31, n-type interconnection wires 32, and metal contacts 33. In the gas sensor 41D, the gas sensing layer 5 is heated by using Peltier effect instead of using Joule heating. The p-type interconnection wires 31 and the n-type interconnection wires 32 are disposed on the support layer 2 and the base layer 3. The p-type interconnection wire 31 and the n-type interconnection wires 32 are provided so as to extend radially from the center of the gas sensor 41D in plan view. The p-type interconnection wire 31 and the n-type interconnection wire 32 are connected to each other with the metal contact 33. The metal contact 33 located under the gas sensing layer 5 can be a metal contact 33b, which is a hot junction. The metal contact 33 exposed on the support layer 2 can be a metal contact 33a, which is a cold junction. The metal contact 33 connects an end of the p-type interconnection wire 31 to an end of the n-type interconnection wire 32. The p-type interconnection wire 31, the n-type interconnection wire 32, and the metal contact 33 are arranged from terminal Heat(+) to terminal Heat(−) in such a way that a plurality of units "p-type interconnection wire 31→metal contact 33b→n-type interconnection wire 32→metal contact 33a" are successively arranged. By applying an electric current in a direction from terminal Heat(+) to terminal Heat(−), the metal contact 33b, which is a hot junction, is heated by the Peltier effect.

In addition, the heater layer 4 can function as a cooling layer by reversing the direction of the electric current applied to the p-type interconnection wire 31, n-type interconnection wire 32, and metal contact 33. Therefore, for example, when the temperature of the environment in which the gas sensor 41D is placed is higher than the set temperature of the gas sensing layer 5, the heater layer 4 can function as a cooling layer, so that the function of the gas sensor can be ensured.

Examples of materials of the p-type interconnection wire 31 and n-type interconnection wire 32 are p-type and n-type doped semiconductors, respectively. Examples of semiconductors are poly-Si and poly-Site. However, the materials that make up the p-type interconnection wire 31 and the n-type interconnection wire 32 are not limited to the above-described examples.

Examples of materials of the metal contact 33 are metals, such as Pt, Al, Ti, and W.

The p-type interconnection wire 31 and/or the n-type interconnection wire 32 may have a fifth phononic crystal structure structured by a plurality of regularly arranged through-holes. In this case, the thermal insulation performance between the substrate 1 and the gas sensing layer 5 can be improved more.

Fourth Embodiment

Figure 21:
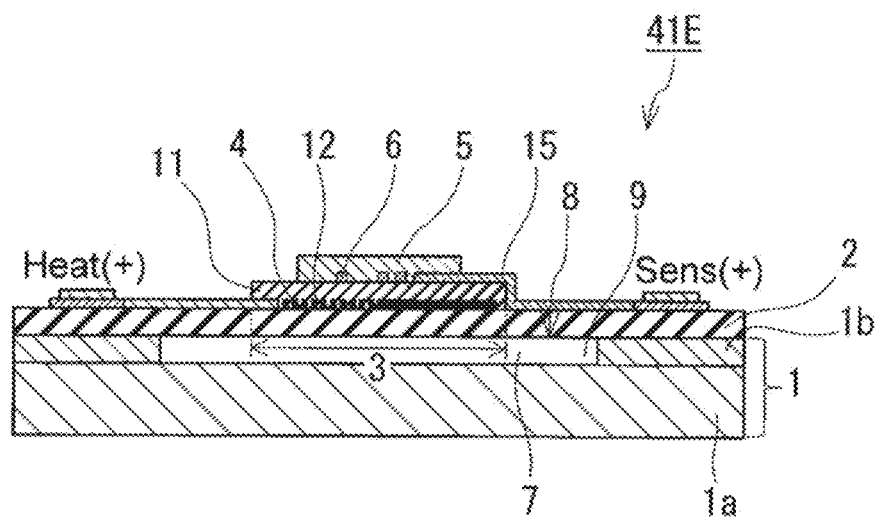
FIG. 21 is a cross-sectional view schematically illustrating a gas sensor according to a fourth embodiment.

FIG. 21 illustrates a gas sensor 41E according to the fourth embodiment. The gas sensor 41E has the same configuration as the gas sensor 41A according to the first embodiment, except for the configurations of the substrate 1 and the cavity 7.

The substrate 1 of the gas sensor 41E has a two-layer structure in which an oxide film 1b is formed on a surface of the base layer 1a. The base layer 1a is formed of the material described above as a material that can constitute the substrate 1. The oxide film 1b is, for example, an $SiO_2$ film.

The cavity 7 of the gas sensor 41E is a part of the substrate 1 corresponding to part of the above-described surface where the oxide film 1b is not formed. The cavity 7 can be formed by removing a portion of the oxide film 1b from the substrate 1 which has the two-layer structure of the base layer 1a and the oxide film 1b. To remove the portion of the oxide film 1b, etching can be used, for example. The etching may be fluorine etching. The portion of the support layer 2 having a phononic crystal structure and the cavity 7 may overlap with or correspond to each other in plan view.

When the cavity 7 is provided after the support layer 2 is disposed, the through-holes provided by the phononic crystal structure of the support layer 2 can be used for etching. Furthermore, additional through-holes for etching may be provided in the support layer 2. The diameter of the through-holes for etching is, for example, greater than or equal to 1000 nm.

In the gas sensor 41E, the through-holes of the phononic crystal structure, especially the first phononic crystal structure of the support layer 2, may be filled with another material. Note that the material of the member 21 having the phononic crystal structure needs to differ from the material in terms of thermal conductivity. By filling the through-holes, stagnation of the gas in the cavity 7 can be prevented, for example.

Fifth Embodiment

Figure 22:
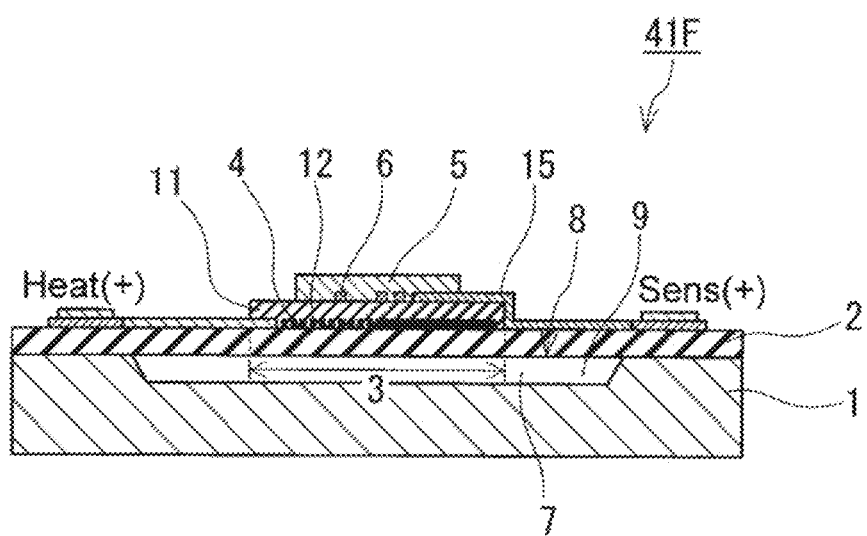
FIG. 22 is a cross-sectional view schematically illustrating a gas sensor according to a fifth embodiment.

FIG. 22 illustrates a gas sensor 41F according to the fifth embodiment. The gas sensor 41F has the same configuration as the gas sensor 41A according to the first embodiment, except for the configuration of the cavity 7.

The cavity 7 of the gas sensor 41F is a recess portion formed on one surface of the substrate 1. The recess portion can be formed by removing a part of the substrate 1. For example, to remove the part, etching can be used. The etching can be crystal anisotropic etching. For crystal anisotropic etching, solution of potassium hydroxide (KOH) or tetramethylammonium hydroxide (TMAH) can be used. The portion of the support layer 2 where the phononic crystal structure is present may overlap with or correspond to the cavity 7 in plan view.

When the cavity 7 is formed after the support layer 2 is disposed, the through-holes of the phononic crystal structure of the support layer 2 can be used for etching. Furthermore, additional through-holes for etching may be provided in the support layer 2. The diameter of the through-holes for etching is, for example, greater than or equal to 1000 nm.

In the gas sensor 41F, the through-holes of the phononic crystal structure, especially the first phononic crystal structure of the support layer 2, may be filled with another material. However, the material of the member 21 having the phononic crystal structure and the material need to be different in terms of thermal conductivity. By filling the through-holes, stagnation of the gas in the cavity 7 can be prevented, for example.

Use Application of Gas Sensor

There is no limit to the use applications of the gas sensor according to the present disclosure. Since the gas sensor according to the present disclosure is a sensor with low power consumption and, thus, can be battery-driven, the gas sensor may be suitably used as a portable or wearable gas sensor. This usage is effective in, for example, the healthcare and environmental monitoring fields. Examples of gas to be measured in the healthcare field include exhaled air and skin gas. Exhaled air and skin gas can be collected in a minimally invasive manner. In addition, for example, by selecting a material of the gas sensing layer 5, a gas sensor that detects the type and/or concentration of various target gases can be achieved. Examples of the target gas include, but not limited to, hydrogen gas, ethanol gas, acetone gas, and isoprene gas. A gas sensor that detects ethanol gas as the target gas can be used, for example, as a sensor for alcohol test which detects the presence of alcohol in breath.

Method for Manufacturing Gas Sensor

The gas sensor according to the present disclosure can be manufactured by a combination of one of various thin film deposition methods, one of various microfabrication and patterning methods, and one of various reformulation methods. Examples of a thin film deposition method include chemical vapor deposition (CVD), sputtering, and vapor deposition. Examples of a microfabrication and patterning method include electron beam lithography, photolithography, block copolymer lithography, and selective etching. Examples of a reformulation method include amorphization by doping and ion implantation, crystallization, and impartation of electroconductivity. Electron beam lithography is suitable to form phononic crystal structures having an alignment period P which is approximately greater than or equal to 100 nm and less than or equal to 300 nm. Block copolymer lithography is suitable to form phononic crystal structures having an alignment period P which is approximately greater than or equal to 1 nm and less than or equal to 100 nm. Note that block copolymer lithography is also suitable to form the phononic crystal structure A.

An example of a method for manufacturing the gas sensor 41A according to the first embodiment is described below. The gas sensors according to the other embodiments can be manufactured in a similar manner. However, a method for manufacturing the gas sensor according to the present disclosure is not limited to the example described below.

An SiN layer that serves as the support layer 2 and the base layer 3 is formed on a Si substrate. The SiN layer can be formed by, for example, CVD. The support layer 2 and the base layer 3 may be $SiO_2$ layer. Subsequently, a phononic crystal structure is formed in the SiN layer. Thereafter, a poly-Si layer is formed on the support layer 2 and the base layer 3. The poly-Si layer has electrical conductivity provided by doped impurity. The poly-Si layer can be formed by, for example, CVD. Subsequently, a patterning process is performed on the poly-Si layer to form the first interconnection wire 13, the resistance heating wire 12, the second interconnection wire 14, and the terminals Heat(+) and Heat(−). The patterning process can be carried out by, for example, reactive ion etching (RIE). Subsequently, an SiN layer is formed on the resistance heating wire 12. Subsequently, the SiN layer is patterned to form the electrically insulating layer 11. Subsequently, a poly-Si layer is formed on the support layer 2, the base layer 3, and the electrically insulating layer 11. Subsequently, a patterning process is performed on the poly-Si layer to form the detection electrode 6, the third interconnection wire 15, the fourth interconnection wire 16, the terminal Sens(+), and the terminal Sens(−). Subsequently, an $SnO_2$ layer is formed on the electrically insulating layer 11 and the detection electrode 6. The $SnO_2$ layer can be formed by, for example, sputtering. Subsequently, a patterning process is performed on the $SnO_2$ layer to form the gas sensing layer 5. Subsequently, the through-hole 10 is formed by etching from the back side of the Si substrate. A gas sensor 41A in which each of the member other than the support layer 2 has a phononic crystal structure can be produced by, for example, inserting a step of forming a phononic crystal structure after each of the members is formed.

Gas Sensor System

The gas sensor according to the present disclosure can be used to construct a gas sensor system. The gas sensor system comprises the gas sensor according to the present disclosure and a control device. The control device supplies electric power to the heater layer 4 of the gas sensor and receives a detection signal output from the detection electrode 6. There is no limit to the configuration of the control device. An publically known technique can be applied to connection between the gas sensor and the control device. The gas sensor system according to the present disclosure can comprise any member in addition to the gas sensor and the control device.

EXAMPLES

The gas sensor according to the present disclosure is described in more detail below with reference to examples. However, the gas sensor according to the present disclosure is not limited to the particular examples described below.

In these examples, the temperature distribution in the gas sensor during heating and the temperature rise of the gas sensing layer during heating are evaluated by simulation. For the simulation, CoventorWare (analysis software available from Coventor, Inc.) is used. The value of an electric current applied to the heater layer in the simulation is set to 2.3 mA (Examples 1 and 2 and Comparative Example 1), 1.5 mA (Examples 3 and 4), or 36 mA (Example 5 and Comparative Example 2). The heat transfer coefficient between the gas sensor and the surrounding air is set to 1 W/(m²·K), which is the cooling condition by natural convection.

The following seven gas sensors are prepared as the gas sensors to be used in the simulation:

Example 1: A gas sensor having the same configuration as the gas sensor 41A illustrated in FIGS. 1A to 2B. However, the gas sensor of Example 1 has a phononic crystal structure only in the portion that overlaps the cavity 7 in the support layer 2 in plan view.

Example 2: A gas sensor having the same configuration as in Example 1, except that the gas sensing layer 5 also has a phononic crystal structure.

Example 3: A gas sensor having the same configuration as in Example 1, except that the resistance heating wire 12 also has a phononic crystal structure.

Example 4: A gas sensor having the same configuration as in Example 1, except that the resistance heating wire 12, the first interconnection wire 13, the second interconnection wire 14, the third interconnection wire 15, and the fourth interconnection wire 16 also have a phononic crystal structure.

Example 5: A gas sensor having the same configuration as in Example 1, except that the materials of the resistance heating wire 12 and the detection electrode 6 differ from each other.

Comparative Example 1: A gas sensor having the same configuration as in Example 1, except that none of the members has a phononic crystal structure, Comparative Example 2: A gas sensor having the same configuration as in Example 5, except that none of the members has a phononic crystal structure.

The following members are used to constitute each of the gas sensors:

Substrate 1: Si substrate

Support layer 2: SiN layer having a thickness of 0.2 μm

Heater layer 4 (resistance heating wire 12): Highly doped poly-Si layer, 0.6-μm thick, resistivity of 1 mΩ·cm without a phononic crystal structure (Examples 1 to 4 and Comparative Example 1), or Pt layer, 0.6 m thick, resistivity of 11 mΩ·cm without a phononic crystal structure (Example 5 and Comparative Example 2)

Electrically insulating layer 11: SiN layer having a thickness of 0.2 μm

Detection electrode 6: highly doped poly-Si layer, 0.4 m thick, resistivity of 1 mΩ·cm without phononic crystal structure Resistivity of 1 mΩ·cm (Examples 1 to 4 and Comparative Example 1), or Pt layer having a thickness of 0.4 μm, resistivity of 11 μΩ·cm without a phononic crystal structure (Example 5 and Comparative Example 2)

First interconnection wire 13, Second interconnection wire 14, Third interconnection wire 15, and Fourth interconnection wire 16: Highly doped poly-Si layer, 0.6 μm thick, resistivity of 1 mΩ·cm without phononic crystal structure Gas sensing layer 5: $SnO_2$ thin film with a thickness of 0.2 μm.

The shape of the gas sensing layer 5 and the electrically insulating layer 11 was set to be a circle with a diameter of 1 mm in plan view. The cavity 7 was set to be a through-hole 10 extending vertically in the thickness direction of the substrate 1 and having a circular cross-section of 2 mm in diameter. The width of each of the interconnection wires 13, 14, 15, and 16 was set to 50 μm.

The phononic crystal structure of the gas sensors in Examples 1 to 5 is structured by through-holes each having a circular cross-section of 75 nm in diameter. The arrangement period P between adjacent through-holes was 100 nm, and the unit lattice of the through-holes is set to a hexagonal lattice.

Figure 23:
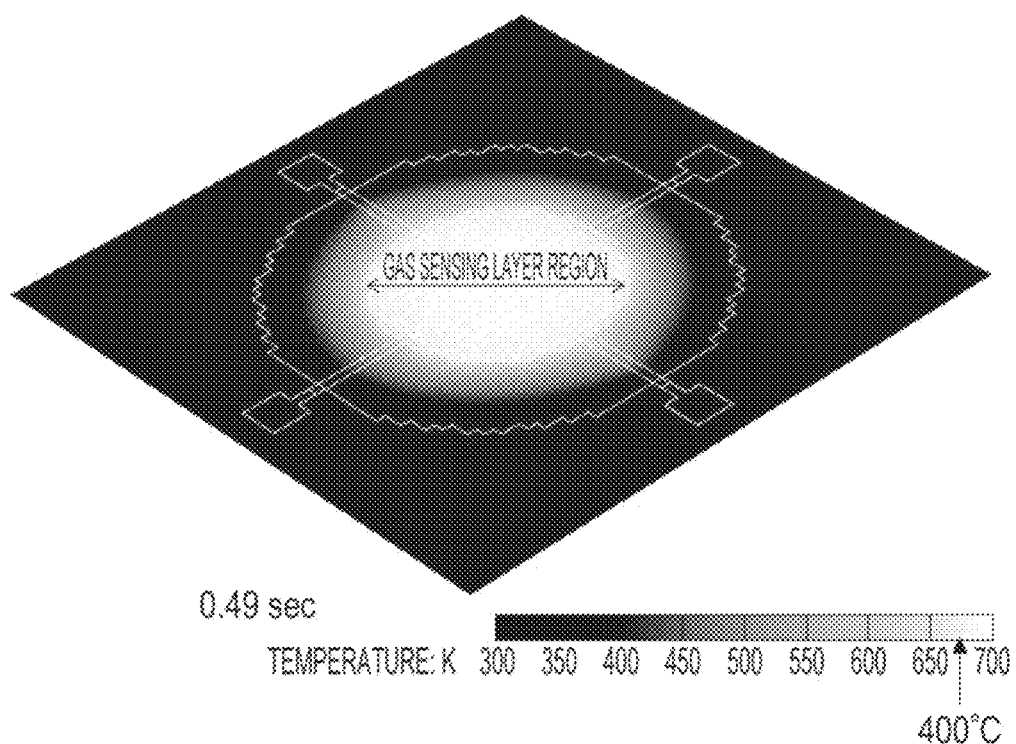
FIG. 23 is a diagram illustrating simulated temperature distribution over the upper surface of a gas sensor according to a comparative example at 0.49 seconds after application of an electric current.

For the gas sensor of Comparative Example 1, simulation of the temperature distribution during heating is performed. The time when a current is applied between the terminals Heat(+) and Heat(−) is set to t=0 seconds, and the temperature distribution of the upper surface of the gas sensor at t=0.49 seconds is illustrated in FIG. 23. As can be seen from FIG. 23, 0.49 seconds after the time of current application, the temperature of the gas sensing layer reaches 400° C.

Figure 24:
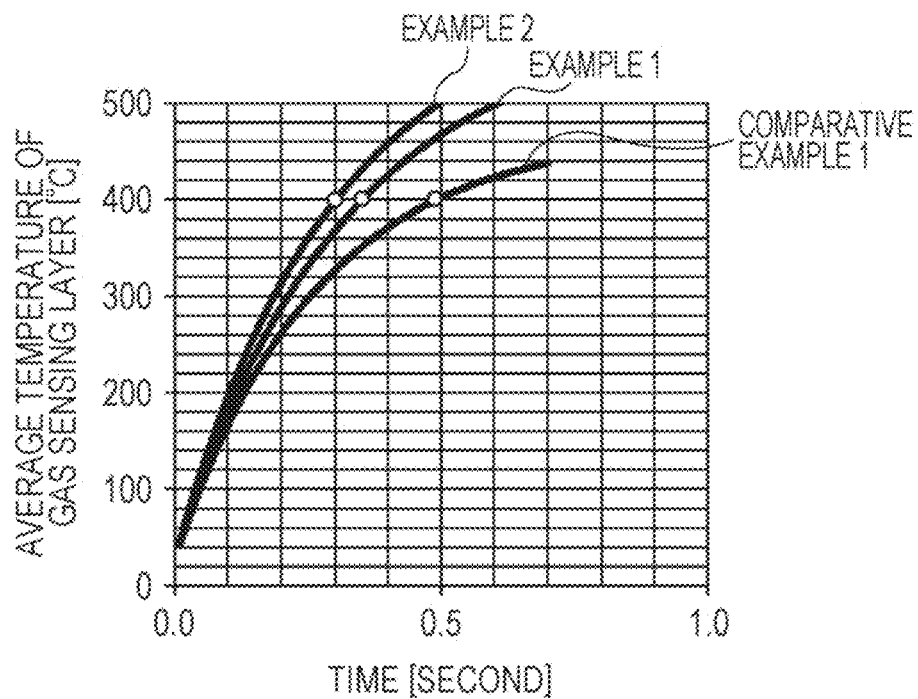
FIG. 24 is a graph illustrating a simulated relationship between the application time of an electric current and the average temperature of the gas sensing layer of a gas sensor in a comparative example and each of examples.

For the gas sensors of Example 1, Example 2, and Comparative Example 1, the relationship between the time of current application and the average temperature of the gas sensing layer is evaluated through the above simulation. The relationship is illustrated in FIG. 24. As described above, in Comparative Example 1, the temperature of the gas sensing layer reaches 400° C. 0.49 seconds after the time of current application. In contrast, in Example 1 in which the support layer 2 has a phononic crystal structure, it takes only 0.35 seconds for the temperature of the gas sensing layer to reach 400° C. That is, the power consumption of the gas sensor of Example 1 can be reduced to 71% of the power consumption of the gas sensor of Comparative Example 1 (=0.35/0.49× 100). In addition, in Example 2 in which the support layer 2 and the gas sensing layer 5 each have a phononic crystal structure, it takes only 0.30 seconds for the temperature of the gas sensing layer to reach 400° C. That is, the power consumption of the gas sensor of Example 2 can be reduced to 61% of the power consumption of the gas sensor of Comparative Example 1 (=030/0.49×100).

Figure 25:
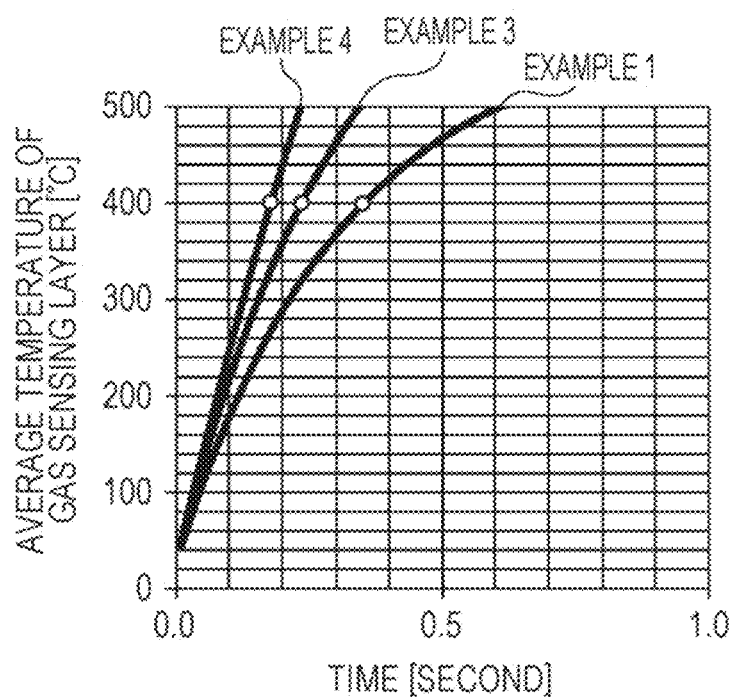
FIG. 25 is a graph illustrating a simulated relationship between the application time of an electric current and the average temperature of the gas sensing layer of a gas sensor in each of examples.

For the gas sensors of Example 1, Example 3, and Example 4, the relationship between the time of current application and the average temperature of the gas sensing layer is evaluated through the above simulation. The relationship is illustrated in FIG. 25. Note that the set value of the current applied to the heater layer in Examples 3 and 4 is 1.5 mA, which differs from the set value of 2.3 mA in Example 1. This is to keep the V×I product between the terminals Heat(+) and Heat(−) constant among Examples in a situation where the electrical conductivity of the resistance heating wire 12 becomes about ⅓ the original due to the phononic crystal structure. In Example 1 in which the support layer 2 has a phononic crystal structure, the temperature of the gas sensing layer reaches 400° C. 0.35 seconds after the time of current application. In contrast, in Example 3 in which the resistance heating wire 12 also has a phononic crystal structure, it takes only 0.24 seconds for the temperature of the gas sensing layer to reach 400° C. In addition, in Example 4 in which the resistance heating wire 12 and each of the interconnection wires also have a phononic crystal structure, it takes only 0.18 seconds for the temperature of the gas sensing layer to reach 400° C. That is, a further reduction in power consumption can be achieved. The above-described results suggest that further design changes, such as optimization of the volume of the gas sensing layer 5, can be made to raise the temperature to 400° C. within a current application time less than or equal to 0.1 seconds.

Figure 26:
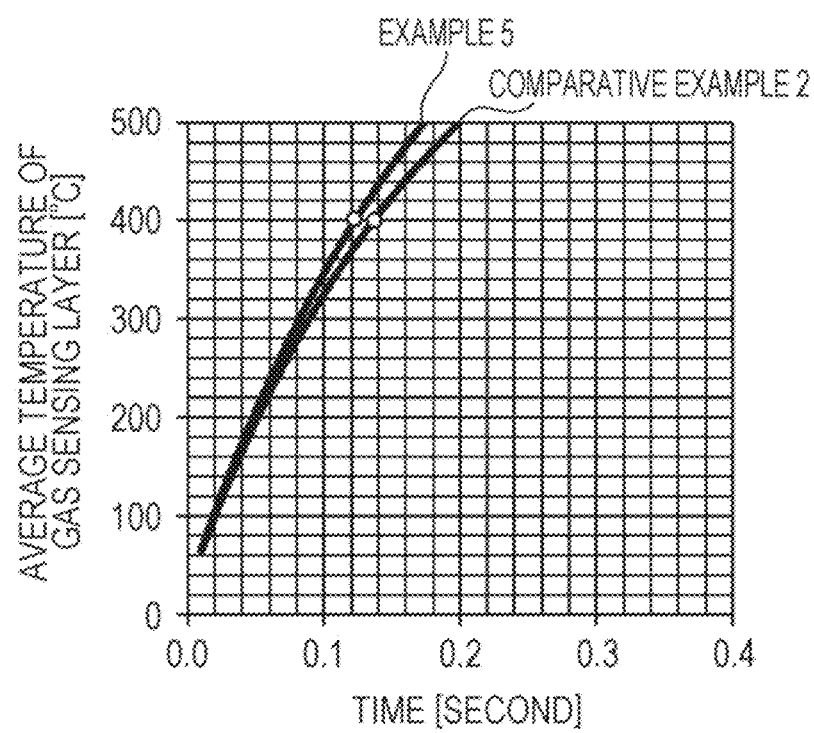
FIG. 26 is a graph denoting a simulated relationship between the application time of an electric current and the average temperature of the gas sensing layer of a gas sensors in a comparative example and an example.

For the gas sensors of Example 5 and Comparative Example 2, the relationship between the time of current application and the average temperature of the gas sensing layer is evaluated through the above simulation. The relationship is illustrated in FIG. 26. As can be seen from FIG. 26, even when the heater layer 4 and the detection electrode 6 are formed of metal, the phononic crystal structure of the support layer 2 enables a temperature rise in the gas sensing layer 5 within a shorter current application time. In Example 5, the temperature of the gas sensing layer reaches 400° C. 0.12 seconds after the time of current application.

The gas sensor according to the present disclosure can be used for a variety of applications, including existing gas sensor applications.

What is claimed is:
1. A gas sensor comprising:
a substrate;
a support layer;
a base layer;
a heater layer disposed on or above the base layer;
a gas sensing layer disposed on or above one of the heater layer and the base layer, the gas sensing layer having an electrical impedance that is gas concentration dependent; and
a detection electrode electrically connected to the gas sensing layer, the detection electrode detecting the impedance of the gas sensing layer,
wherein the substrate has a cavity,
wherein the substrate has an opening formed by the cavity in plan view,
wherein the support layer is disposed on the substrate so as to cover at least an entire periphery of the opening,
wherein the base layer is supported by the support layer above the cavity so as to be separated from the substrate, and
wherein the support layer has a first phononic crystal structure in a portion in contact with the cavity, and the first phononic crystal structure is structured by a plurality of regularly arranged through-holes.

2. The gas sensor according to claim 1, wherein the gas sensing layer is disposed on or above the heater layer.

3. The gas sensor according to claim 1, further comprising:
an electrically insulating layer,
wherein the electrically insulating layer is disposed between the heater layer and the detection electrode.

4. The gas sensor according to claim 1, wherein the gas sensing layer has a second phononic crystal structure structured by a plurality of regularly arranged through-holes.

5. The gas sensor according to claim 1, wherein the heater layer comprises a resistance heating wire, and
wherein the gas sensor further comprises a first interconnection wire and a second interconnection wire each electrically connected to the resistance heating wire and each supplying an electric current to the resistance heating wire.

6. The gas sensor according to claim 5, wherein the resistance heating wire has a third phononic crystal structure structured by a plurality of regularly arranged through-holes.

7. The gas sensor according to claim 5, wherein the first interconnection wire and/or the second interconnection wire has a fourth phononic crystal structure structured by a plurality of regularly arranged through-holes.

8. The gas sensor according to claim 1, wherein the heater layer is a Peltier element layer including a p-type interconnection wire, an n-type interconnection wire, and a metal contact.

9. The gas sensor according to claim 8, wherein the p-type interconnection wire and/or the n-type interconnection wire have a fifth phononic crystal structure structured by a plurality of regularly arranged through-holes.

10. The gas sensor according to claim 1, further comprising:
a third interconnection wire and a fourth interconnection wire that are electrically connected to the detection electrode and that transmit a detection signal output from the detection electrode.

11. The gas sensor according to claim 10, wherein the third interconnection wire and/or the fourth interconnection wire have a sixth phononic crystal structure structured by a plurality of regularly arranged through-holes.

12. The gas sensor according to claim 1, wherein the first phononic crystal structure includes a first domain and a second domain that are phononic crystal domains,
wherein the first domain is formed by a plurality of through-holes regularly arranged in a first direction in plan view, and
wherein the second domain is formed by a plurality of through-holes regularly arranged in a second direction that differs from the first direction in plan view.

13. The gas sensor according to claim 1, wherein the substrate has a through-hole that connects both principal surfaces of the substrate to each other, and the through-hole functions as the cavity.

14. A gas sensor system comprising:
the gas sensor according to claim 1, and
a supply circuit that supplies electrical power to the heater layer of the gas sensor and a detection circuit that receives a detection signal output from the detection electrode.

15. A gas sensor comprising:
a substrate;
a support layer;
a base layer;
a heater layer disposed on or above the base layer;
a gas sensing layer disposed on or above one of the heater layer and the base layer, the gas sensing layer having an electrical impedance that is gas concentration dependent; and
a detection electrode electrically connected to the gas sensing layer, the detection electrode detecting the impedance of the gas sensing layer,
wherein the substrate has a cavity,
wherein the substrate has an opening formed by the cavity in plan view,
wherein the support layer is disposed on the substrate so as to cover at least part of the periphery of the opening,
wherein the base layer is supported by the support layer above the cavity so as to be separated from the substrate, and wherein the support layer has a first phononic crystal structure in a portion in contact with the cavity, and the first phononic crystal structure is structured by a plurality of regularly arranged through-holes.

* * * * *